US007960415B2

(12) United States Patent
Brenchley et al.

(10) Patent No.: US 7,960,415 B2
(45) Date of Patent: Jun. 14, 2011

(54) CASPASE INHIBITORS AND USES THEREOF

(75) Inventors: Guy Brenchley, West Hanney (GB);
Jean-Damien Charrier, Wantage (GB);
Steven Durrant, Abingdon (GB);
Ronald Knegtel, Abingdon (GB);
Michael Mortimore, Burford (GB);
John Studley, Witney (GB)

(73) Assignee: Vertex Pharmaceutical Incoporated, Cambridge, MA (US)

( * ) Notice: Subject to any disclaimer, the term of this patent is extended or adjusted under 35 U.S.C. 154(b) by 0 days.

(21) Appl. No.: 12/140,497

(22) Filed: Jun. 17, 2008

(65) Prior Publication Data

US 2009/0093416 A1 Apr. 9, 2009

Related U.S. Application Data

(63) Continuation of application No. 10/855,699, filed on May 27, 2004, now abandoned.

(60) Provisional application No. 60/473,622, filed on May 27, 2003.

(51) Int. Cl.
A61K 31/44 (2006.01)
C07D 211/72 (2006.01)
(52) U.S. Cl. ........................................ 514/349; 546/290
(58) Field of Classification Search .................. 546/308, 546/290; 514/352, 349
See application file for complete search history.

(56) References Cited

U.S. PATENT DOCUMENTS

| 4,728,647 | A | 3/1988 | Benavides et al. |
| 5,656,627 | A | 8/1997 | Bemis et al. |
| 5,716,929 | A | 2/1998 | Bemis et al. |
| 5,756,466 | A | 5/1998 | Bemis et al. |
| 5,847,135 | A | 12/1998 | Bemis et al. |
| 5,874,424 | A | 2/1999 | Batchelor et al. |
| 5,973,111 | A | 10/1999 | Bemis et al. |
| 6,025,147 | A | 2/2000 | Bemis et al. |
| 6,103,711 | A | 8/2000 | Bemis et al. |
| 6,184,244 | B1 | 2/2001 | Karanewsky et al. |
| 6,197,750 | B1 | 3/2001 | Karanewsky et al. |
| 6,242,422 | B1 | 6/2001 | Karanewsky et al. |
| 6,420,522 | B1 | 7/2002 | Bemis et al. |
| 6,525,076 | B1 | 2/2003 | Zhu et al. |
| 2003/0162993 | A1 | 8/2003 | Mortimore et al. |
| 2003/0232846 | A1 | 12/2003 | Golec et al. |
| 2004/0019017 | A1 | 1/2004 | Mortimore et al. |
| 2004/0048797 | A1 | 3/2004 | Miller et al. |
| 2004/0072850 | A1 | 4/2004 | Knegtel et al. |
| 2004/0192612 | A1 | 9/2004 | Charrier et al. |
| 2004/0242494 | A1 | 12/2004 | Brenchley et al. |
| 2007/0155718 | A1 | 7/2007 | Durrant et al. |

FOREIGN PATENT DOCUMENTS

| DE | 232699 | 2/1986 |
| EP | 058633 B1 | 8/1992 |
| EP | 0528633 B1 | 8/1992 |
| EP | 0509769 B1 | 9/1996 |
| EP | 0761680 A2 | 12/1997 |
| EP | 1203766 A2 | 5/2002 |
| EP | 0826671 B1 | 12/2004 |
| GB | 2292149 | 2/1996 |
| WO | 9316710 A1 | 9/1993 |
| WO | 9321210 A1 | 10/1993 |
| WO | 9526958 A1 | 10/1995 |
| WO | 9535308 A2 | 12/1995 |
| WO | 9603982 A1 | 2/1996 |
| WO | 9640647 A1 | 12/1996 |
| WO | 9816502 A1 | 4/1998 |
| WO | 9816505 A1 | 4/1998 |
| WO | 9818781 A2 | 5/1998 |
| WO | 0023421 A1 | 4/2000 |
| WO | 0061542 A1 | 10/2000 |
| WO | 0067746 A1 | 11/2000 |
| WO | 0068188 A1 | 11/2000 |
| WO | 0142216 A2 | 6/2001 |
| WO | 0194351 A1 | 12/2001 |
| WO | 03024955 A2 | 3/2003 |
| WO | 03042169 | 5/2003 |
| WO | 03068242 | 8/2003 |
| WO | 2004002961 A1 | 1/2004 |
| WO | 2004058718 A1 | 7/2004 |
| WO | 2004106304 A2 | 12/2004 |
| WO | 2006057961 A1 | 6/2006 |

(Continued)

OTHER PUBLICATIONS

Semple, et al., "Pyridone-Based Peptidomimetic Inhibitors of Interleukin-1Beta-Converting Enzyme (ICE)," Bioorganic & Medicinal Chemistry Letters, 7(10):1337-1342 (1997).
Livingston, et al., "In Vitro and In Vivo Studies of ICE Inhibitors," Journal of Cellular Biochemistry, 64:19-26 (1997).
Husain, et al., "Some New 2-Aryloxymethyl-3-alpha-substituted Carboxymethyl-6, 8-Substituted-4-quinazolones as Possible Anticonvulsants," Pharmazie, 37:408-410 (1982).
Hussain, et al., "Some Newer Quinazolones as Possible Anticonvulsants," J. Chem. Soc. Pak., 6(4):211-215 (1984).
Canonne, et al., "Synthesis of Chiral 3-Substituted 2,4 (1H, 3H)-Quinazolinediones," Heterocycles, 36(6):1305-1314 (1993).

(Continued)

Primary Examiner — Janet L Andres
Assistant Examiner — Heidi Reese
(74) Attorney, Agent, or Firm — Jennifer G. Che; Vertex Pharmaceuticals Incorporated

(57) ABSTRACT

The present invention provides a compound of formula I:

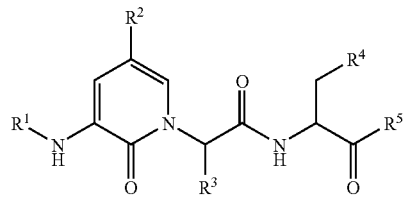

wherein $R^1$, $R^2$, $R^3$, $R^4$, and $R^5$ are as defined herein. The present invention also provides pharmaceutical compositions and methods using such compositions for treating a caspase-mediated diseases and processes for preparing the compounds of the invention.

9 Claims, No Drawings

FOREIGN PATENT DOCUMENTS

| WO | 2007015931 A2 | 2/2007 |
|----|---------------|--------|
| WO | 9722619 A2 | 6/2009 |

OTHER PUBLICATIONS

Warner, et al., "Non-peptidic Inhibitors of Human Leukocyte Elastase. 1. The Design and Synthesis of Pyridone-Containing Inhibitors," J. Med. Chem., 37(19), 3090-3099 (1994).
Gouilleux, et al., "Solid Phase Synthesis of chiral 3-substituted Quinazoline-2, 4-diones," Tetrahedron Letters, 37 (39):7031-7034 (1996).
Gordeev, et al., "A General and Efficient Solid Phase Synthesis of Quinazoline-2, 4-diones," Tetrahedron Letters, 38 (10):1729-1732 (1997).
Talanian, et al., "Caspase as Targets for Anti-Inflammatory and Anti-Apoptotic Drug Discovery," Journal of Medicinal Chemistry, 43(18):3351-3371 (2000).
Lalonde, et al., "Use of a Papain as a Model for the Structure-Based Design of Cathepsin K Inhibitors: Crystal Structures of Two Papain-Inhibitor Complexes Demonstrate Binding to S'-Subsites", J. Med. Chem., 41:4567-4576 (1998).
Mjalli, et al. "Inhibition of Interleukin-1beta Converting Enzyme By N-Acyl-Aspartic Acid Ketones", Bioorganic & Medicinal Chemistry Letters, 5 (13);1405-1408 (1995).
Dolle, et al. "Aspartyl alpha-((Diphenylphosphinyl)oxy)methyl Ketones as Novel Inhibitors of Interleukin-1beta Converting Enzyme, Utility of the Diphenylphosphinic Acid Leaving Group for the Inhibition of Cysteine Proteases" J. Med. Chem. 38:220-222 (1995).
Dolle et al, "First Examples of Peptidomimetic Inhibitors of Interleukin-1 Converting Enzyme" J. Med. Chem vol. 39, pp. 2438-2440 (1996).
Patani et al., "Bioisosterism: A Rational Approach in Drug Design", Chem. Rev., 96(8), 3147-3176, (1996).
Golec et al, "Structure-based design of Non-peptidic Pyridone Aldehydes as Inhibitors of Interleukin-1β-Converting Enzyme" Bioorganic & Medicinal Chem. Letters, 7(17):2181-2186 (1997).
Semple et al. "Peptidomimetic Aminomethylene Ketone Inhibitors of Interleukin-1β-Converting Enzyme (ICE)", Bioorganic & medicinal Chemistry Letters, 8:959-964, (1998).
Witek et al. "Pan-Caspase Inhibitor VX-166 Reduces Fibrosis in an Animal Model of Nonalcoholic Steatohepatitis", Hepatology, 50(10):1-10, (2009).
Weber et al. "VX-166: A Novel potent small molecule caspase inhibitor as a potential therapy for sepsis", Crisitcal Care, 13(5), 1-11, (2009).
Veale, et al., "Nonpeptidic Inhibitors of Human Leukocyte Elastase, 5 Design, Synthesis and X-Ray Crystallography of a serieds of Orally Active 5-Aminopyrimidin-6-one Containing Trufluorometheyl Ketones", J. Med. Chem., 38(1), 98-108, (1995).
Damewood, James R., et al., "Nonpeptidic Inhibitors of Human Leukocyte Elastase. 2. Design, Synthesis, and in Vitro Activity of a Series of 3-Amino-6-arylopyridin-2-one Trifluoromethyl Ketones", J. Med. Chem., 37, 303-3312, (1994).
Erlanson et al., "In situ assembly of enzyme inhibitors using extended tethering" Nature Biotechnology, 21 (3):308-314, (2003).
Dragovich, Peter S., et al., "Structure-based design, synthesis, and biological evaluation of irreversible human rhinovirus 3C protease inhibitors. 6. Structure-activity studies of orally bioavailable , 2-pyridone-containing peptidomimetics", J. Med. Chem., 45,1607-1623, (2002).
Ellis et al., "Mechanisms and functions of cell death", Annual review cell biology, 7, 663, (1991).
Yaoita, Hiroyuki et al., "Attenuation of ischemia/reperfusion injury in rats by a caspase inhibitor", Circulation, 97, 276-281 (1998).
Cheng,Yu et al., "Caspase inhibitor affords neuroprotection with delayed administration in a rat model of neonatal hypoxic-ischemic brain injury", Journal of Clinical Investigation, 101, 1992-1999 (1998).
Yakovlev, Alexander G. et al., "Activation of CPP32-like caspases contributes to neuronal apoptosis and neurological dysfunction after traumatic brain injury", The Journal of Neuroscience, 17, 7415-7424, (1997).
Rodriguez, Ivan et al., "Systemic injection of a tripeptide inhibits the intracellular activation of CPP32-like proteases in vivo and fully protects mice against fas-mediated fulminant liver destruction and death", Journal of Experimental Medicine,184, 2067-2072, (1996).
Grobmyer et al., "Peptidomimetic fluoromethylketone rescues mice from lethal endotoxic shock", 5, 585, (1999).
Plattner, JJ et al., "Obstacles to Drug Development from Peptide Leads", Drug Discovery Technologies, 93-126, (1990).
Golstein, Pierre, "Cell Death in Us and Others", Science, 281, 1283-1284, (1998).
Rano, Thomas et al., "A combinatorial approach for determining protease specificites: application to interleukin-1β converting enzyme (ICE)", Chemistry & Biology, 2, 4, 149-155, (1997).
Mjalli, Adnan M.M. et al., "Phenylalkyl ketones as potent reversible inhibitors of interleukin-1β converting enzyme", Bioorganic & Medicinal Chemistry Letters, 3, 12, 2689-2692, (1993).
Endres, Matthias et al., "Attenuation of delayed neuronal death after mild focal ischemia in mice by inhibition of the caspase family", Journal of Cerebral Blood Flow and Metabolism,18, 238-247, (1998).
Narasimhan, R.S. "Synthetic Application of Lithiation Reactions; IX. A Simplified Synthesis of Isocoumarin," Synthesis, 12(797), (1975).
Revesz, L., et al. "Synthesis of P1 Aspartate-Based Peptide Acyloxymethyl and Fluoromethyl Ketones as Inhibitors of Interleukin-1β-Converting Enzyme," Tetrahedron Letters, 35(52): 9693-9696,(1994). .
Thornberry, Nancy A., "Key mediators of apoptosis", Chemical Biology, 5, R97-R103, (1998).
Wilson, Keith et al., "Structure and mechanism of interleukin-1β converting enzyme", Nature, 370, 270-275, (1994).
Lazebnik et al., "Cleavage of poly(ADP-ribose) polymerase by a proteinase with properties like ICE", Nature, 371, 346-347, (1994).
Greig, Nigel H. et al., "Physicochemical and pharmacokinetic parameters of seven lipophilic chlorambucil esters designed for brain penetration", Cancer Chemother. Pharmacol., 25, 311-319, (1990).
Tejani-Butt, Shanaz M. et al., "Evaluation of mono-and dibenzoyl esters of dopamine as potential pro-drugs for dopamine in the central nervous system", Arch. Pharmacol., 338(5), 497-503, (1988).
Prokai-Tatrai, Katalin et al., "Brain-targeted delivery of a leucine-enkephalin analogue by retrometabolic design", J. Med. Chem., 39, 4775-4782, (1996).
Toyoaki, Ishikura, et al., "Drug delivery to the brain. DOPA prodrugs based on a ring-closure reaction to quaternary thiazolium compounds", Int. J. Pharmaceuticals, 116, 51-63, (1995).
Paolo, Bonina, Francesco et al., "Synthesis, stability, and pharmacological evaluation of nipecotic acid prodrugs", Pharma. Sci., 88(5), 561-567, (1999).
Battaglia, G. et al., "Systemically administered d-glucose conjugates of 7-chlorokynurenic acid are centrally available and exert anticonvulsant activity in rodents", Brain Res., 860, 149-156, (2000).
Prokai-Tatrai, K. et al., "Prodrugs to Enhance Central Nervous System Effects of TRH-like Peptide pGlu-Glu-Pro-NH2," Bioorg. Med. Chem. Lett., 13,1011-1014, (2003).
Kinder, M. A., et al. "Solid State Photochemistry of Isocoumarins and Isothiocoumarins," Tetrahedron 56, 6763-6767 (2000).
Caba, Josep M. et al., "Solid-phase total synthesis of trunkamide A 1", J. Org. Chem., 66, 7568-7574, (2001).
Schierle, Gabrielle S. et al., "Caspase inhibition reduces apoptosis and increases survival of nigral transplants", Nature Medicine, 5, 97-100, (1999).
Anderson, B.D., "Prodrugs for improved CNS delivery", Advanced Drug Delivery Reviews, 19, 171-202, (1996).
Schwab, John H. et al., "Pro-and Anti-Inflammatory Roles of Interleukin-1 in Recurrence of Bacterial Cell Wall-Induced Arthritis in Rats", Infection and Immunity, 59(12), 4436-4442, (1991).
Estrov, Zeev et al., "Suppression of Chronic Myelogenous Leukemia Colony Growth by Interleukin-1 (IL-1) Receptor Antagonist and Soluble IL-1 Receptors: A Novel Application for Inhibitors of IL-1 Activity", Blood, 78(6), 1476-1484, (1991).
Estrov, Zeev et al., "Inhibition of Acute Myelogenous Leukemia Blast Proliferation by Interleukin-1 (IL-1) Receptor Antagonist and Soluble IL-1 Receptors", Blood, 79(8), 1938-1945, (1992).

Rouquet, Nicolas et al., "ICE Inhibitor YVADcmk is a potent therapeutic agent against in vivo liver apoptosis", Current Biology, 6(9), 1192-1195, (1996).

Miller, Bruce E. et al., "Inhibition of Mature IL-1β Production in Murine Macrophages and a Murine Model of Inflammation by WIN 67694, an Inhibitor of IL-1β Converting Enzyme", Journal of Immunology, 154, 1331-1338, (1995).

Kuida, Keisuke et al., "Alteres Cytokine Export and Apoptosis in Mice Deficient in Interleukin-1β Converting Enzyme", Science, 267, 2000-2003, (1995).

Ku, George et al., "Interleukin-1β Converting Enzyme Inhibition Blocks Progression of Type II Collagen-Induced Arthritis in Mice", 8(5), 377-386, (1996).

Bernstein, Peter et al., "Preparation of N-(oxoalkyl)-5-(acylamino)-6-oxopyrimidin-1-ylacetamides as elastase inhibitors", Chemical Abstracts, 119, No. 72617, (1993).

Bernstein, Peter et al., "Aminopyrimidinyl acetamide elastase inhibitors", Chemical Abstracts, 120, No. 217713, (1994).

Medline Abstract for, "Annals of the Academy of Medicine", 27(5), 738-743, (1998).

Cominelli, Fabio et al., "Interleukin 1 (IL-1) Gene Expression, Synthesis, and Effect of Specific IL-1 Receptor Blockade in Rabbit Immune Complex Colitis", J. Clin. Invest., 86, 972-980, (1990).

Li, Ping et al., "Mice Deficient in IL-1β-Converting Enzyme are Defective in Production of Mature IL-1β and Resistant to Endotoxic Shock", Cell, 80, 401-411, (1995).

Miller, Laurie C. et al., "Balance of synovial fluid IL-1β and IL-1 receptor antagonist and recovery from Lyme arthritis", Lancet, 341, 146-148, (1993).

Miller, Douglas K., "The IL-1β Converting Enzyme as a Therapeutic Target", Science, 696, 133-148, (1993).

Geiger, T., et al., "Neutralization of interleukin-1β activity in vivo with a monoclonal antibody alleviates collagen-induced arthritis in DBA/1 mice and prevents the associated acute-phase response", Clinical and Experimental Rheumatology, 11, 515-522, (1993).

CASPASE INHIBITORS AND USES THEREOF

Pursuant to Title 35, United States Code §120, this application is a continuation of U.S. patent application Ser. No. 10/855,699, filed May 27, 2004, now abandoned, which claims the benefit of U.S. Provisional Application No. 60/473,622, filed May 27, 2003.

FIELD OF THE INVENTION

This invention is in the field of medicinal chemistry and relates to compounds, and pharmaceutical compositions thereof, that inhibit caspases that mediate cell apoptosis and inflammation. The invention also relates to processes for preparing these compounds. The invention further relates to methods of using the compounds and pharmaceutical compositions of this invention to treat diseases where caspase activity is implicated.

BACKGROUND OF THE INVENTION

Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, ischemic diseases and certain neurodegenerative disorders (see generally *Science*, 1998, 281, 1283-1312; Ellis et al., *Ann. Rev. Cell. Biol.,* 1991, 7, 663).

Caspases are a family of cysteine protease enzymes that are key mediators in the signaling pathways for apoptosis and cell disassembly (Thornberry, *Chem. Biol.,* 1998, 5, R97-R103). These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

Caspase-1, the first identified caspase, is also known as interleukin converting enzyme or "ICE." Caspase-1 converts precursor interleukin-1β("pIL-1β") to the pro-inflammatory active form by specific cleavage of pIL-1β between Asp-116 and Ala-117. Besides caspase-1 there are also eleven other known human caspases, all of which cleave specifically at aspartyl residues. They are also observed to have stringent requirements for at least four amino acid residues on the N-terminal side of the cleavage site.

The caspases have been classified into three groups depending on the amino acid sequence that is preferred or primarily recognized. The group of caspases, which includes caspases 1, 4, 5 and 13, have been shown to prefer hydrophobic aromatic amino acids at position 4 on the N-terminal side of the cleavage site. Another group which includes caspases 2, 3 and 7, recognize aspartyl residues at both positions 1 and 4 on the N-terminal side of the cleavage site, and preferably a sequence of Asp-Glu-X-Asp. A third group, which includes caspases 6, 8, 9 and 10, tolerate many amino acids in the primary recognition sequence, but seem to prefer residues with branched, aliphatic side chains such as valine and leucine at position 4.

The caspases have also been grouped according to their perceived function. The first subfamily consists of caspases-1 (ICE), 4, 5 and 13. These caspases have been shown to be involved in pro-inflammatory cytokine processing and therefore play an important role in inflammation. Caspase-1, the most studied enzyme of this class, activates the IL-1β precursor by proteolytic cleavage. This enzyme therefore plays a key role in the inflammatory response. Caspase-1 is also involved in the processing of interferon-γ inducing factor (IGIF, also known as IL-18) which stimulates the production of interferon gamma, a key immunoregulator that modulates antigen presentation, T-cell activation and cell adhesion.

The remaining caspases make up the second and third subfamilies. These enzymes are of central importance in the intracellular signaling pathways leading to apoptosis. One subfamily consists of the enzymes involved in initiating events in the apoptotic pathway, including transduction of signals from the plasma membrane. Members of this subfamily include caspases-2, 8, 9 and 10. The other subfamily, consisting of the effector capsases 3, 6 and 7, are involved in the final downstream cleavage events that result in the systematic breakdown and death of the cell by apoptosis. Caspases involved in the upstream signal transduction activate the downstream caspases, which then disable DNA repair mechanisms, fragment DNA, dismantle the cell cytoskeleton and finally fragment the cell.

Knowledge of the four amino acid sequence primarily recognized by the caspases has been used to design caspase inhibitors. Reversible tetrapeptide inhibitors have been prepared having the structure $CH_3CO$—[P4]-[P3]-[P2]—$CH(R)CH_2CO_2H$ where P2 to P4 represent an optimal amino acid recognition sequence and R is an aldehyde, nitrile or ketone capable of binding to the caspase cysteine sulfhydryl. Rano and Thornberry, *Chem. Biol.* 4, 149-155 (1997); Mjalli, et al., *Bioorg. Med. Chem. Lett.* 3, 2689-2692 (1993); Nicholson et al., *Nature* 376, 37-43 (1995). Irreversible inhibitors based on the analogous tetrapeptide recognition sequence have been prepared where R is an acyloxymethylketone —$COCH_2OCOR'$. R' is exemplified by an optionally substituted phenyl such as 2,6-dichlorobenzoyloxy and where R is $COCH_2X$ where X is a leaving group such as F or Cl. Thornberry et al., *Biochemistry* 33, 3934 (1994); Dolle et al., *J. Med. Chem.* 37, 563-564 (1994).

The utility of caspase inhibitors to treat a variety of mammalian disease states associated with an increase in cellular apoptosis has been demonstrated using peptidic caspase inhibitors. For example, in rodent models caspase inhibitors have been shown to reduce infarct size and inhibit cardiomyocyte apoptosis after myocardial infarction, to reduce lesion volume and neurological deficit resulting from stroke, to reduce post-traumatic apoptosis and neurological deficit in traumatic brain injury, to be effective in treating fulminant liver destruction, and to improved survival after endotoxic shock. Yaoita et al., *Circulation,* 97, 276 (1998); Endres et al., *J Cerebral Blood Flow and Metabolism,* 18, 238, (1998); Cheng et al., *J. Clin. Invest.,* 101, 1992 (1998); Yakovlev et al., *J Neuroscience,* 17, 7415 (1997); Rodriquez et al., *J. Exp. Med.,* 184, 2067 (1996); Grobmyer et al., *Mol. Med.,* 5, 585 (1999).

In general, the peptidic inhibitors described above are very potent against some of the caspase enzymes. However, this potency has not always been reflected in cellular models of apoptosis. In addition peptide inhibitors are typically characterized by undesirable pharmacological properties such as poor oral absorption, poor stability and rapid metabolism. Plattner and Norbeck, in *Drug Discovery Technologies,* Clark and Moos, Eds. (Ellis Horwood, Chichester, England, 1990).

Recognizing the need to improve the pharmacological properties of the peptidic caspase inhibitors, peptidomimetic inhibitors have been reported. Amongst these, inhibitors where the P3 amino acid has been replaced by derivatives of 3-aminopyridin-2-ones and 5-aminopyrimidin-4-ones have been reported (U.S. Pat. No. 5,756,466 (Bemis et al.); PCT Publication No. WO 95/35308 (Bemis et al.); Dolle et al. *J. Med. Chem.* 39, 2438, (1996); Golec et al. *Bioorg. Med. Chem. Lett.* 7, 2181, (1997); Semple et al, *Biorg. Med. Chem. Lett.* 7, 1337, (1997)).

Due to the inherent problems of the peptidic inhibitors, there continues to be a need for small molecule, nonpeptide caspase inhibitors that are potent, stable, and penetrate membranes to provide effective inhibition of apoptosis in vivo. Such compounds would be extremely useful in treating the aforementioned diseases where caspase enzymes play a role.

SUMMARY OF THE INVENTION

The present invention provides a compound of formula I:

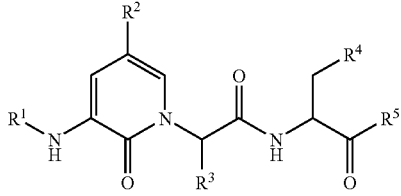

I wherein: $R^1$, $R^2$, $R^3$, $R^4$, and $R^5$ are as defined herein.

The present invention also provides pharmaceutical compositions comprising a compound of formula I and methods using such compounds and compositions for treating caspase-mediated diseases. The present invention also provides processes for preparing the compounds of formula I.

DETAILED DESCRIPTION OF THE INVENTION

The present invention provides a compound of formula I:

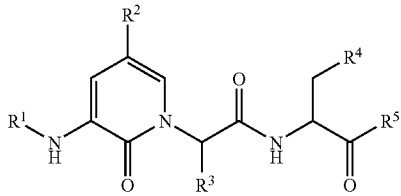

I wherein:
$R^1$ is $R^6C(O)$—, $HC(O)$—, $R^6SO_2$—, $R^6OC(O)$—, $(R^6)_2NC(O)$—, $(R^6)(H)NC(O)$—, $R^6C(O)C(O)$—, $R^6$—, $(R^6)_2NC(O)C(O)$—, $(R^6)(H)NC(O)C(O)$—, or $R^6C(O)C(O)$—;

$R^2$ is hydrogen, —$CF_3$, halo, —$OR^7$, —$NO_2$, —$OCF_3$, —CN, or $R^8$;

$R^3$ is hydrogen or (C1-C4)-aliphatic-;

$R^4$ is —COOH or —$COOR^8$;

$R^5$ is —$CH_2F$ or —$CH_2O$-2,3,5,6-tetrafluorophenyl;

$R^6$ is (C1-C12)-aliphatic-(C3-C10)-cycloaliphatic-, (C6-C10)-aryl-, (C3-C10)-heterocyclyl-, (C5-C10)-heteroaryl-, (C3-C10)-cycloaliphatic-(C1-C12)-aliphatic-, (C6-C10)-aryl-(C1-C12)-aliphatic-, (C3-C10)-heterocyclyl-(C1-C12)-aliphatic-, (C5-C10)-heteroaryl(C1-C12)-aliphatic-, or two $R^6$ groups bound to the same atom form together with that atom a 3- to 10-membered aromatic or nonaromatic ring; wherein the ring is optionally fused to a (C6-C10)aryl, (C5-C10)heteroaryl, (C3-C10)cycloalkyl, or a (C3-C10)heterocyclyl; wherein up to 3 aliphatic carbon atoms may be replaced by a group selected from O, N, N(R), S, SO, and $SO_2$; and wherein $R^6$ is substituted with up to 6 substituents independently selected from R;

R is halogen, —$OR^7$, —$OC(O)N(R^7)_2$, —$NO_2$, —CN, —$CF_3$, —$OCF_3$, —$R^7$, oxo, thioxo, =$NR^7$, =$N(OR^7)$, 1,2-methylenedioxy, 1,2-ethylenedioxy, —$N(R^7)_2$, —$SR^7$, —$SOR^7$, —$SO_2R^7$, —$SO_2N(R^7)_2$, —$SO_3R^7$, —$C(O)R^7$, —$C(O)C(O)R^7$, —$C(O)C(O)OR^7$, —$C(O)C(O)N(R^7)_2$, —$C(O)CH_2C(O)R^7$, —$C(S)R^7$, —$C(S)OR^7$, —$C(O)OR^7$, —$OC(O)R^7$, —$C(O)N(R^7)_2$, —$OC(O)N(R^7)_2$, —$C(S)N(R^7)_2$, —$(CH_2)_{0-2}NHC(O)R^7$, —$N(R^7)N(R^7)COR^7$, —$N(R^7)N(R^7)C(O)OR^7$, —$N(R^7)N(R^7)CON(R^7)_2$, —$N(R^7)SO_2R^7$, —$N(R^7)SO_2N(R^7)_2$, —$N(R^7)C(O)OR^7$, —$N(R^7)C(O)R^7$, —$N(R^7)C(S)R^7$, —$N(R^7)C(O)N(R^7)_2$, —$N(R^7)C(S)N(R^7)_2$, —$N(COR^7)COR^7$, —$N(OR^7)R^7$, —$C(=NH)N(R^7)_2$, —$C(O)N(OR^7)R^7$, —$C(=NOR^7)R^7$, —$OP(O)(OR^7)_2$, —$P(O)(R^7)_2$, —$P(O)(OR^7)_2$, or —$P(O)(H)(OR^7)$;

two $R^7$ groups together with the atoms to which they are bound form a 3- to 10-membered aromatic or non-aromatic ring having up to 3 heteroatoms independently selected from N, N(R), O, S, SO, or $SO_2$, wherein the ring is optionally fused to a (C6-C10)aryl, (C5-C10)heteroaryl, (C3-C10)cycloalkyl, or a (C3-C10)heterocyclyl, and wherein any ring has up to 3 substituents selected independently from $J_2$; or each $R^7$ is independently selected from:

hydrogen-, (C1-C12)-aliphatic-, (C3-C10)-cycloaliphatic-, (C3-C10)-cycloaliphatic-(C1-C12)-aliphatic-, (C6-C10)-aryl-, (C6-C10)-aryl-(C1-C12)aliphatic-, (C3-C10)-heterocyclyl-, (C6-C10)-heterocyclyl-(C1-C12)aliphatic-, (C5-C10)-heteroaryl-, or (C5-C10)-heteroaryl-(C1-C12)-aliphatic-;

wherein $R^7$ has up to 3 substituents selected independently from $J_2$; and $J_2$ is halogen, —$OR^7$, —$OC(O)N(R^7)_2$, —$NO_2$, —CN, —$CF_3$, —$OCF_3$, —$R^7$, oxo, thioxo, =$NR^7$, =$NOR^7$, 1,2-methylenedioxy, 1,2-ethylenedioxy, —$N(R^7)_2$, —$SR^7$, —$SOR^7$, —$SO_2R^7$, —$SO_2N(R^7)_2$, —$SO_3R^7$, —$C(O)R^7$, —$C(O)C(O)R^7$, —$C(O)C(O)OR^7$, —$C(O)C(O)N(R^7)_2$, —$C(O)CH_2C(O)R^7$, —$C(S)R^7$, —$C(S)OR^7$, —$C(O)OR^7$, —$OC(O)R^7$, —$C(O)N(R^7)_2$, —$OC(O)N(R^7)_2$, —$C(S)N(R^7)_2$, —$(CH_2)_{0-2}NHC(O)R^7$, —$N(R^7)N(R^7)COR^7$, —$N(R^7)N(R^7)C(O)OR^7$, —$N(R^7)N(R^7)CON(R^7)_2$, —$N(R^7)S_2R^7$, —$N(R^7)SO_2N(R^7)_2$, —$N(R^7)C(O)OR^7$, —$N(R^7)C(O)R^7$, —$N(R^7)C(S)R^7$, —$N(R^7)C(O)N(R^7)_2$, —$N(R^7)C(S)N(R^7)_2$, —$N(COR^7)COR^7$, —$N(OR^7)R^7$, —CN, —$C(=NH)N(R^7)_2$, —$C(O)N(OR^7)R^7$, —$C(=NOR^7)R^7$, —$OP(O)(OR^7)_2$, —$P(O)(R^7)_2$, —$P(O)(OR^7)_2$, or —$P(O)(H)(OR^7)$; and $R^8$ is (C1-C12)-aliphatic-(C3-C10)-cycloaliphatic-, (C6-C10)-aryl-, (C3-C10)-heterocyclyl-, (C5-C10)-heteroaryl-, (C3-C10)-cycloaliphatic-(C1-C12)-aliphatic-, (C6-C10)-aryl-(C1-C12)-aliphatic-, (C3-C10)-heterocyclyl-(C1-C12)-aliphatic-, or (C5-C10)-heteroaryl(C1-C12)-aliphatic-, wherein up to 3 aliphatic carbon atoms may be replaced with a group selected from O, N, N(R), S, SO, and $SO_2$; and wherein $R^8$ is optionally substituted with up to 6 substituents independently selected from R.

The present invention also provides a compound of formula I:

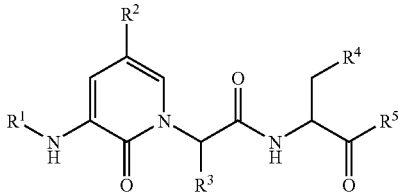

wherein:
R¹ is R⁶C(O)—, R⁶SO₂—, R⁶OC(O)—, (R⁶)₂NC(O)—, R⁶C(O)C(O)—, R⁶—, (R⁶)₂NC(O)C(O)—, or R⁶OC(O)C(O)—;
R² is hydrogen, —CF₃, halo, —OR⁷, —NO₂, —OCF₃, —CN, or R⁸;
R³ is hydrogen or (C1-C4)-aliphatic-;
R⁴ is —COOH or —COOR⁸;
R⁵ is —CH₂F or —CH₂O-2,3,5,6-tetrafluorophenyl;
R⁶ is (C1-C12)-aliphatic-(C3-C10)-cycloaliphatic-, (C6-C10)-aryl-, (C3-C10)-heterocyclyl-, (C5-C10)-heteroaryl-, (C3-C10)-cycloaliphatic-(C1-C12)-aliphatic-, (C6-C10)-aryl-(C1-C12)-aliphatic-, (C3-C10)-heterocyclyl-(C1-C12)-aliphatic-, (C5-C10)-heteroaryl(C1-C12)-aliphatic-, or two R⁶ groups bound to the same atom form together with that atom a 3- to 10-membered aromatic or nonaromatic ring; wherein the ring is optionally fused to a (C6-C10)aryl, (C5-C10)heteroaryl, (C3-C10)cycloalkyl, or a (C3-C10)heterocyclyl; wherein up to 3 aliphatic carbon atoms may be replaced by a group selected from O, N(H), N(R), S, SO, and SO₂; and wherein R⁶ is substituted with up to 6 substituents independently selected from R;
R is halogen, —OR⁷, —OC(O)N(R⁷)₂, —NO₂, —CN, —CF₃, —OCF₃, —R⁷, oxo, thioxo, 1,2-methylenedioxy, 1,2-ethylenedioxy, —N(R⁷)₂, —SR⁷, —SOR⁷, —SO₂R⁷, —SO₂N(R⁷)₂, —SO₃R⁷, —C(O)R⁷, —C(O)C(O)R⁷, —C(O)CH₂C(O)R⁷, —C(S)R⁷, —C(O)OR⁷, —OC(O)R⁷, —C(O)N(R⁷)₂, —OC(O)N(R⁷)₂, —C(S)N(R⁷)₂, —(CH₂)₀₋₂NHC(O)R⁷, —N(R⁷)N(R⁷)COR⁷, —N(R⁷)N(R⁷)C(O)OR⁷, —N(R⁷)N(R⁷)CON(R⁷)₂, —N(R⁷)SO₂R⁷, —N(R⁷)SO₂N(R⁷)₂, —N(R⁷)C(O)OR⁷, —N(R⁷)C(O)R⁷, —N(R⁷)C(S)R⁷, —N(R⁷)C(O)N(R⁷)₂, —N(R⁷)C(S)N(R⁷)₂, —N(COR⁷)COR⁷, —N(OR⁷)R⁷, —C(=NH)N(R⁷)₂, —C(O)N(OR⁷)R⁷, —C(=NOR⁷)R⁷, —OP(O)(OR⁷)₂, —P(O)(R⁷)₂, —P(O)(OR⁷)₂, or —P(O)(H)(OR⁷);
two R⁷ groups together with the atoms to which they are bound form a 3- to 10-membered aromatic or non-aromatic ring having up to 3 heteroatoms independently selected from N(H), N(R), O, S, SO, or SO₂, wherein the ring is optionally fused to a (C6-C10)aryl, (C5-C10)heteroaryl, (C3-C10)cycloalkyl, or a (C3-C10)heterocyclyl, and wherein any ring has up to 3 substituents selected independently from J₂; or
each R⁷ is independently selected from:
hydrogen-,
(C1-C12)-aliphatic-,
(C3-C10)-cycloaliphatic-,
(C3-C10)-cycloaliphatic-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic-,
(C5-C10)-heteroaryl-, or
(C5-C10)-heteroaryl-(C1-C12)-aliphatic-;
wherein R⁷ has up to 3 substituents selected independently from J₂; and
J₂ is halogen, —OR⁷, —OC(O)N(R⁷)₂, —NO₂, —CN, —CF₃, —OCF₃, —R⁷, oxo, thioxo, 1,2-methylenedioxy, 1,2-ethylenedioxy, —N(R⁷)₂, —SR⁷, —SOR⁷, —SO₂R⁷, —SO₂N(R⁷)₂, —SO₃R⁷, —C(O)R⁷, —C(O)C(O)R⁷, —C(O)CH₂C(O)R⁷, —C(S)R⁷, —C(O)R⁷, —OC(O)R⁷, —C(O)N(R⁷)₂, —OC(O)N(R⁷)₂, —C(S)N(R⁷)₂, —(CH₂)₀₋₂NHC(O)R⁷, —N(R⁷)N(R⁷)COR⁷, —N(R⁷)N(R⁷)C(O)OR⁷, —N(R⁷)N(R⁷)CON(R⁷)₂, —N(R⁷)SO₂R⁷, —N(R⁷)SO₂N(R⁷)₂, —N(R⁷)C(O)OR⁷, —N(R⁷)C(O)R⁷, —N(R⁷)C(S)R⁷, —N(R⁷)C(O)N(R⁷)₂, —N(R⁷)C(S)N(R⁷)₂, —N(COR⁷)COR⁷, —N(OR⁷)R⁷, —CN, —C(=NH)N(R⁷)₂, —C(O)N(OR⁷)R⁷, —C(=NOR⁷)R⁷, —OP(O)(OR⁷)₂, —P(O)(R⁷)₂, —P(O)(OR⁷)₂, or —P(O)(H)(OR⁷); and
R⁸ is (C1-C12)-aliphatic-(C3-C10)-cycloaliphatic-, (C6-C10)-aryl-, (C3-C10)-heterocyclyl-, (C5-C10)-heteroaryl-, (C3-C10)-cycloaliphatic-(C1-C12)-aliphatic-, (C6-C10)-aryl-(C1-C12)-aliphatic-, (C3-C10)-heterocyclyl-(C1-C12)-aliphatic-, or (C5-C10)-heteroaryl(C1-C12)-aliphatic-, wherein up to 3 aliphatic carbon atoms may be replaced with a group selected from O, N(H), N(R), S, SO, and SO₂.

Another embodiment of this invention provides a compound wherein, R¹ is R⁶C(O)—, R⁶SO₂—, or R⁶—. In a preferred embodiment, R¹ is R⁶C(O)—. In another preferred embodiment, R¹ is R⁶SO₂—. In yet another preferred embodiment, R¹ is R⁶—.

Another embodiment of this invention provides a compound wherein R¹ is (R⁶)₂NC(O)— or (R⁶)OC(O)—. In a preferred embodiment, R¹ is (R⁶)₂NC(O)—. In another preferred embodiment, R¹ is (R⁶)(H)NC(O)—. In yet another preferred embodiment, R¹ is (R⁶)OC(O)—.

In one embodiment of this invention, each R⁶ is independently (C1-C4)-aliphatic-, (C3-C10)-cycloaliphatic, (C3-C10)-heterocyclyl, (C5-C10)-heteroaryl, (C6-C10)-aryl-, or (C6-C10)-aryl-(C1-C12)-(it being understood that optionally up to 3 aliphatic carbon atoms may be replaced by a group selected from O, N, N(R), S, SO, and SO₂; and wherein R⁶ is optionally substituted with up to 6 substituents independently selected from R or R⁶ is substituted as disclosed in any of the embodiments herein).

In another embodiment, each R⁶ is independently H, (C1-C4)-aliphatic- or (C6-C10)-aryl- or each R⁶ together with the N-atom is a (C3-C7)-cycloaliphatic.

In another embodiment, each R⁶ is independently (C1-C4)-aliphatic-, (C5-C10)-heteroaryl-, or (C6-C10)-aryl-, wherein the heteroaryl or aryl is optionally substituted or wherein each R⁶ together with the N-atom is a (C3-C7)-cycloaliphatic group.

In another embodiment, each R⁶ is independently (C1-C4)-aliphatic- or (C6-C10)-aryl-, wherein the aryl is optionally substituted or wherein each R⁶ together with the N-atom is a (C3-C7)-cycloaliphatic.

In yet another embodiment, each R⁶ is independently (C1-C4)-aliphatic-, (C3-C7)-cycloaliphatic, (C6-C10)-aryl-, (C5-C10)-heteroaryl, wherein the heteroaryl and aryl are independently and optionally substituted, or each R⁶ together with the N-atom is a (C3-C7)-cycloaliphatic.

According to a preferred embodiment of this invention, R² is hydrogen, C1-, C2-, C3-, or C4-alkyl-, —CF₃, —Cl, —OR⁷, —NO₂, —OCF₃, or —CN. More preferably, R² is hydrogen, C1-alkyl-, C2-alkyl-, or CF₃. More preferably, R² is hydrogen or CF₃.

According to another preferred embodiment, R³ is ethyl.

According to another preferred embodiment, $R^5$ is —CH$_2$O-2,3,5,6-tetrafluorophenyl.

According to another preferred embodiment, $R^5$ is —CH$_2$F.

According to another preferred embodiment, $R^8$ is (C1-C12)-alkyl. More preferably, $R^8$ is (C1-C4)-alkyl.

According to a preferred embodiment, each R and $J_2$ are independently halogen, —OR$^7$, —OC(O)N(R$^7$)$_2$, —NO$_2$, —CN, —CF$_3$, —OCF$_3$, —R$^7$, oxo, 1,2-methylenedioxy, 1,2-ethylenedioxy, —N(R$^7$)$_2$, —C(O)R$^7$, —C(O)C(O)R$^7$, —C(O)OR$^7$—OC(O)R$^7$, —C(O)N(R$^7$)$_2$, or —OC(O)N(R$^7$)$_2$.

As used herein, the carbon atom designations may have the indicated integer and any intervening integer. For example, the number of carbon atoms in a (C1-C4)-alkyl group is 1, 2, 3, or 4. It should be understood that these designation refer to the total number of atoms in the appropriate group. For example, in a (C3-C10)-heterocyclyl the total number of carbon atoms and heteroatoms is 3 (as in aziridine), 4, 5, 6 (as in morpholine), 7, 8, 9, or 10.

As used herein, an aliphatic group includes straight-chained and branched groups having the specified number of atoms. If the number of atoms is unspecified, the aliphatic group has from 1 to 12 carbon atoms. As would be understood, alkenyl and/or alkynyl aliphatic groups have a minimum of 2 carbon atoms. Preferred aliphatic groups are alkyl groups (preferably having from 1 to 6 atoms).

Accordingly, unless otherwise specified, preferred aliphatic groups of this invention are alkyl groups and have 1, 2, 3, 4, 5, or 6 carbon atoms. More preferred alkyl groups have 1, 2, 3, or 4 carbon atoms. Preferred alkenyl and alkynyl groups of this invention have 2, 3, 4, 5, or, 6 carbon atoms and more preferably, from 2, 3, or 4 carbon atoms.

Cycloalkyl and cycloalkenyl groups have between 3 and 10 carbon atoms and are monocyclic or bicyclic, including linearly fused, bridged, or spirocyclic. A cycloaliphatic group is, preferably, a cycloalkyl or a cylcoalkenyl. More preferred cycloaliphatic groups are 3-, 4-, 5-, 6-, or 7-membered rings that are, more preferably, cycloalkyl rings.

As used herein, "aromatic group" or "aryl" refers to a 6-10-membered ring system that contains at least one aromatic ring. Example of aromatic rings include phenyl and naphthyl.

As used herein a "heteroaryl" refers to ring system having 5-10 members and 1, 2, or 3 heteroatoms independently selected from N, N(R), O, S, SO, and SO$_2$, wherein at least one ring is heteroaromatic (e.g., pyridyl, thiophene, or thiazole). Preferred heteroaryl groups are 5- or 6-membered rings having 1 or 2 heteroatoms. In certain embodiments of this invention, more preferred heteroaryl groups are those that have contain a "=N" group.

Examples of heteroaryl rings include 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As used herein a "heterocycle" refers to ring system having 3-10 members and 1, 2, or 3 heteroatoms independently selected from N, N(R), O, S, SO, and SO$_2$, wherein no ring is aromatic (e.g., piperidine and morpholine). Preferred heterocyclyl groups are 5- or 6-membered rings having 1 or 2 heteroatoms.

Examples of heterocyclic rings include 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Any of these cycloaliphatic, heterocyclyl, and heteroaryl groups are optionally fused with a 5- or 6-membered aryl or heteroaryl ring. Furthermore, each of any aliphatic, aryl, cycloaliphatic, heteroaryl, and heterocyclyl may contain appropriate substituents (preferably up to 5, more preferable up to 3, and even more preferably, 0 or 1) independently selected from, for example, carbonyl and R. Preferred substituents (including R and $J_2$) are halogen, —OR$^7$, —NO$_2$, —CF$_3$, —OCF$_3$, —R$^7$, oxo, —OR$^7$, —O-benzyl, —O-phenyl, 1,2-methylenedioxy, 1,2-ethylenedioxy, —N(R$^7$)$_2$, —C(O)R$^7$, —COOR$^7$ or —CON(R$^7$)$_2$, wherein R$^7$ is defined herein (and is preferably H, (C1-C6)-alkyl, or (C2-C6)-alkenyl and alkynyl), with (C1-C6)-alkyl being most preferred). It should be understood that this definition would include a perfluorinated alkyl group.

In embodiments of this invention where R is a substituent on a nitrogen atom, preferred R groups are selected from the group consisting of —R$^7$, —SOR$^7$, —SO$_2$R$^7$, —SO$_2$N(R$^7$)$_2$, —SO$_3$R$^7$, —C(O)R$^7$, —C(O)C(O)R$^7$, —C(O)C(O)OR$^7$, —C(O)C(O)N(R$^7$)$_2$, —C(O)CH$_2$C(O)R$^7$, —C(S)R$^7$, —C(S)OR$^7$, —C(O)OR$^7$, —C(O)N(R$^7$)$_2$, —C(S)N(R$^7$)$_2$, —(CH$_2$)$_{0-2}$NHC(O)R$^7$, —N(R$^7$)N(R$^7$)COR$^7$—N(R$^7$)N(R$^7$)C(O)OR$^7$, —N(R$^7$)N(R$^7$)CON(R$^7$)$_2$, —N(R$^7$)SO$_2$R$^7$, —N(R$^7$)SO$_2$N(R$^7$)$_2$, —N(R$^7$)C(O)OR$^7$, —N(R$^7$)C(O)R$^7$, —N(R$^7$)C(S)R$^7$—N(R$^7$)C(O)N(R$^7$)$_2$, —N(R$^7$)C(S)N(R$^7$)$_2$, —N(COR$^7$)COR$^7$, —N(OR$^7$)R$^7$, —C(=NH)N(R$^7$)$_2$, —C(O)N(OR$^7$)R$^7$—C(=NOR$^7$)R$^7$, —OP(O)(OR$^7$)$_2$, —P(O)(R$^7$)$_2$, —P(O)(OR$^7$)$_2$, and —P(O)(H)(OR$^7$), wherein R$^7$ is defined herein (and is preferably H, (C1-C6)-alkyl, or (C2-C6)-alkenyl and alkynyl), with (C1-C6)-alkyl being most preferred). More preferably, such R groups are selected from the group consisting of —R$^7$ and —C(O)R$^7$.

In preferred compounds of this invention, the stereochemistry is as depicted below:

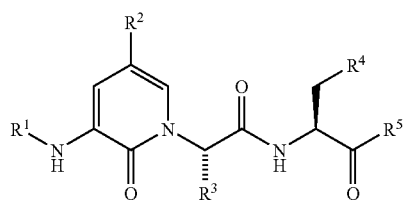

I

Any of the embodiments disclosed herein may be combined to provide alternative embodiments of this invention. Specific embodiments of this invention may be selected from the substituents depicted in the compounds of Table 1

The compounds of the present invention are broad caspase inhibitors and have an improved ability over reported compounds to inhibit apoptosis (see Examples 42 and 43).

According to a preferred embodiment, this invention provides a compound of formula Ia or Ib

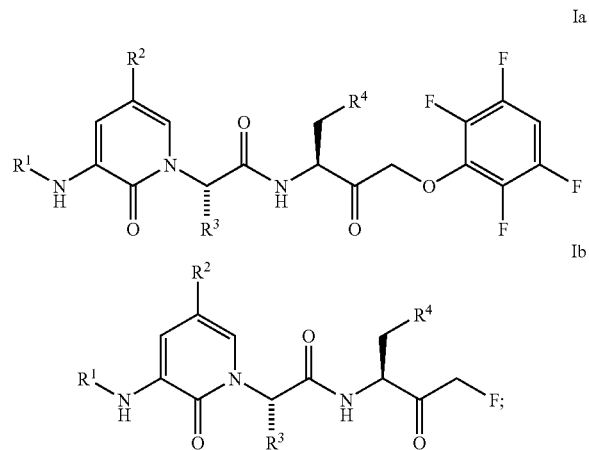

wherein $R^1$, $R^2$, $R^3$, and $R^4$ are as defined in any of the embodiments herein.

According to a more preferred embodiment, the compound of formula I of present invention provides a compound of formula II, selected from Table 1 below:

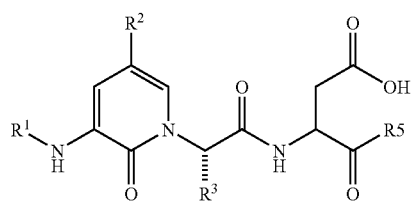

TABLE 1

| Ex. | $R^1$ | $R^2$ | $R^3$ | $R^5$ |
|---|---|---|---|---|
| 1 | Me(C=O)— | H | Et | $CH_2$O-2,3,5,6-tetrafluorophenyl |
| 2 | Et(C=O)— | H | Et | $CH_2$O-2,3,5,6-tetrafluorophenyl |
| 3 | n-Pr(C=O)— | H | Et | $CH_2$O-2,3,5,6-tetrafluorophenyl |
| 4 | c-Pr(C=O)— | H | Et | $CH_2$O-2,3,5,6-tetrafluorophenyl |
| 5 | i-Pr(C=O)— | H | Et | $CH_2$O-2,3,5,6-tetrafluorophenyl |
| 6 | MeOCH$_2$(C=O)— | H | Et | $CH_2$O-2,3,5,6-tetrafluorophenyl |
| 7 | 2-Furyl(C=O)— | H | Et | $CH_2$O-2,3,5,6-tetrafluorophenyl |
| 8 | 3-Furyl(C=O)— | H | Et | $CH_2$O-2,3,5,6-tetrafluorophenyl |
| 9 | 3-Pyridyl(C=O)— | H | Et | $CH_2$O-2,3,5,6-tetrafluorophenyl |
| 10 | 3-Isothiazole(C=O) | H | Et | $CH_2$O-2,3,5,6-tetrafluorophenyl |
| 11 | Ph(C=O)— | H | Et | $CH_2$O-2,3,5,6-tetrafluorophenyl |
| 12 | Bn(C=O)— | H | Et | $CH_2$O-2,3,5,6-tetrafluorophenyl |
| 13 | Me(C=O)— | $CF_3$ | Et | $CH_2$O-2,3,5,6-tetrafluorophenyl |
| 14 | EtNH(C=O)— | H | Et | $CH_2$O-2,3,5,6-tetrafluorophenyl |
| 15 | (Et)$_2$N(C=O)— | H | Et | $CH_2$O-2,3,5,6-tetrafluorophenyl |
| 16 | Pyrrolidinyl-(C=O)— | H | Et | $CH_2$O-2,3,5,6-tetrafluorophenyl |
| 17 | MeO(C=O)— | H | Et | $CH_2$O-2,3,5,6-tetrafluorophenyl |
| 18 | Et(SO$_2$)— | H | Et | $CH_2$O-2,3,5,6-tetrafluorophenyl |
| 19 | n-Pr(SO$_2$)— | H | Et | $CH_2$O-2,3,5,6-tetrafluorophenyl |
| 20 | i-Pr(SO$_2$)— | H | Et | $CH_2$O-2,3,5,6-tetrafluorophenyl |
| 21 | Ph(SO$_2$)— | H | Et | $CH_2$O-2,3,5,6-tetrafluorophenyl |
| 22 | Et(SO$_2$)— | $CF_3$ | Et | $CH_2$O-2,3,5,6-tetrafluorophenyl |
| 23 | Bn(C=O)— | H | i-Pr | $CH_2$O-2,3,5,6-tetrafluorophenyl |
| 24 | Et(SO$_2$) | H | i-Pr | $CH_2$O-2,3,5,6-tetrafluorophenyl |
| 25 | Et(C=O) | H | Me | $CH_2$F |
| 26 | Ph(C=O)— | H | Me | $CH_2$F |
| 27 | 2,6-DiClPh(C=O) | H | Me | $CH_2$F |
| 28 | Bn(C=O)— | H | Me | $CH_2$F |
| 29 | Et(C=O)— | H | Et | $CH_2$F |
| 30 | Ph(C=O)— | H | Et | $CH_2$F |
| 31 | 2,6-DiClPh(C=O) | H | Et | $CH_2$F |
| 32 | 2-Pyridyl(C=O)— | H | Et | $CH_2$F |
| 33 | Bn(C=O)— | H | Et | $CH_2$F |
| 34 | 3-MeBn(C=O)— | H | Et | $CH_2$F |
| 35 | Et(C=O)— | H | n-Pr | $CH_2$F |
| 36 | Et(C=O)— | H | i-Bu | $CH_2$F |
| 37 | Bn(C=O)— | Me | Et | $CH_2$F |
| 38 | Thiazol-2-yl | H | Et | $CH_2$O-2,3,5,6-tetrafluorophenyl |
| 39 | n-Propyl | H | Et | $CH_2$O-2,3,5,6-tetrafluorophenyl |

According to another embodiment, the present invention provides a pharmaceutical composition comprising:

a) a compound of formula I, as defined herein, or a pharmaceutically acceptable salt thereof; and b) a pharmaceutically acceptable carrier, adjuvant or vehicle.

It will be apparent to one skilled in the art that certain compounds of this invention may exist in tautomeric forms or hydrated forms, all such forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

The compounds of this invention may be prepared in general by methods known to those skilled in the art for analogous compounds and by the preparative examples that follow. For the purposes of illustration, the following Schemes I-II for the synthesis of the compounds of the present invention are provided. It should be understood that any protective group depicted in the schemes may be varied as appropriate in view of compatibility with other substituents.

Various protecting groups may be used in the methods of this invention (see, e.g., T. W. Greene & P. G. M Wutz, "Protective Groups in Organic Synthesis", 3$^{rd}$ Edition, John Wiley & Sons, Inc. (1999) and the earlier editions of this book). Typical functional groups that must be protected are amines. Any amines and other functional groups may be protected according to methods known in the art. Compounds, including amines, may be used with or without isolation from the reaction mixtures.

Scheme I

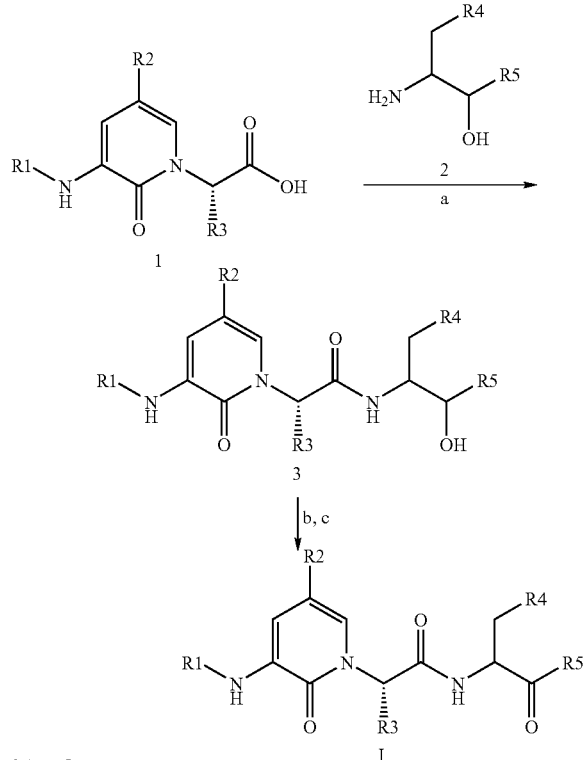

Scheme I
(a) EDC/DMAP/HOBt/THF;
(b) Dess-Martin periodinane;
(c) TFA/DCM

In Scheme I above, the following abbreviations are used: EDC is 1-(3-dimethylaminopropyl)-3-ethylcarbodiimide; HOBt is 1-hydroxybenzotriazole; THF is tetrahydrofuran; TFA is trifluoroacetic acid; DCM is dichloromethane; DMAP is 4-dimethylaminopyridine. Acid 1 is coupled to amino alcohol 2. Here the coupling is depicted using EDC/DMAP/HOBt/THF, however, other suitable conditions may also be used. Depending on the nature of $R^4$ and $R^5$ an amino ketone may be used, in place of the amino alcohol, thus avoiding the subsequent oxidation step. In the case of fluoromethyl ketones where $R^5$ is $CH_2F$, the amino alcohol 2 may be obtained according to the method of Revesz et al., *Tetrahedron Lett.* 1994, 35, 9693. In the case of tetrafluorophenoxy ketones where $R^5$ is —$CH_2O$-2,3,5,6-tetrafluorophenyl, amino alcohol 2 may be obtained by methods analogous to those of Semple et al., *Bioorganic and Medicinal Chemistry Letters*, 1997, 7, 1337 (Scheme II).

Finally the hydroxy group in compound 3 is oxidized (e.g., with Dess-Martin periodinane) and the resulting compound treated appropriately according to the nature of $R^4$. For example, in product I if $R^4$ is a carboxylic acid, then $R^4$ in 3 is preferably an ester that is hydrolyzed in the final step of the scheme. If that ester is a t-butyl ester (i.e., if $R^4$ is $CO_2tBu$), treatment with trifluoroacetic acid will give the acid. The ester is preferably a t-butyl ester when the other substituents in I are compatible with acidic conditions.

If $R^4$ in product I is an ester, the desired ester may be prepared by esterifying the corresponding acid or by having the desired ester group already present in compound 2.

Scheme II

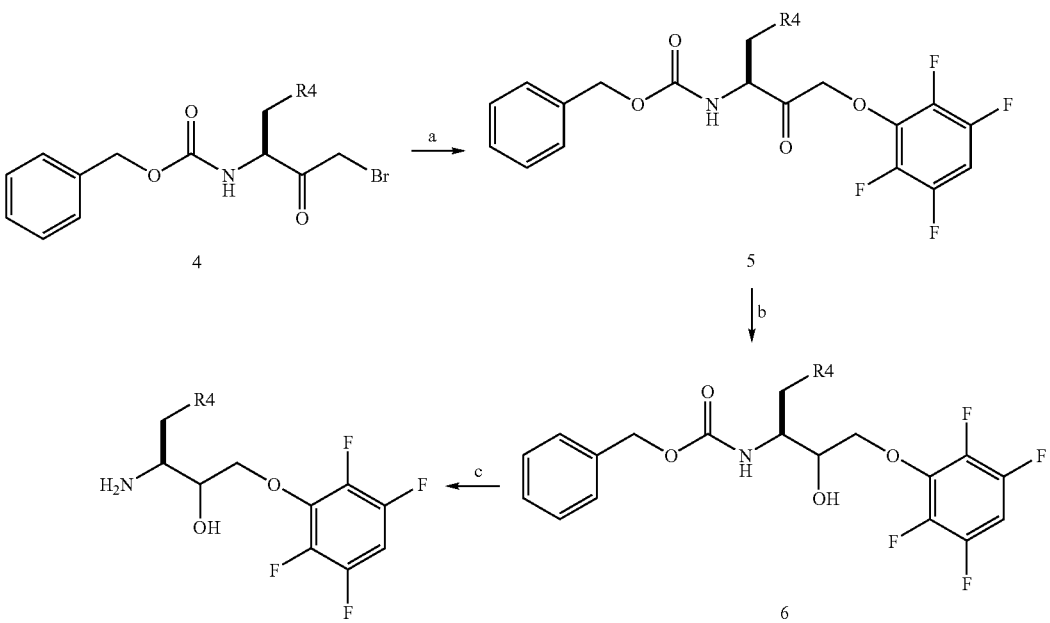

Scheme II
(a) KF/DMF/ArOH;
(b) NaBH$_4$/THF;
(c) H$_2$/Pd/C/MeOH

In scheme II above, the following abbreviations are used: KF is potassium fluoride; DMF is N,N-dimethylformamide; ArOH is 2,3,5,6-tetrafluorophenol; THF is tetrahydrofuran; MeOH is methanol. Commercially available bromoketone 4 ($R^4$=$CO_2$tBu) is reacted with 2,3,5,6-tetrafluorophenol and potassium fluoride to give phenoxy ketone 5. The ketone is then reduced with, for example, sodium borohydride to give the alcohol 6, which is hydrogenated by using, for example, palladium on carbon as catalyst to give the amino alcohol 2 ($R^4$=$CO_2$tBu, $R^5$=$CH_2$O-2,3,5,6-tetrafluorophenyl).

Therefore, another embodiment of this invention provides a process for preparing a compound of formula I:

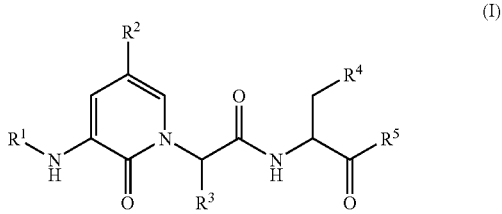

(I)

Scheme III

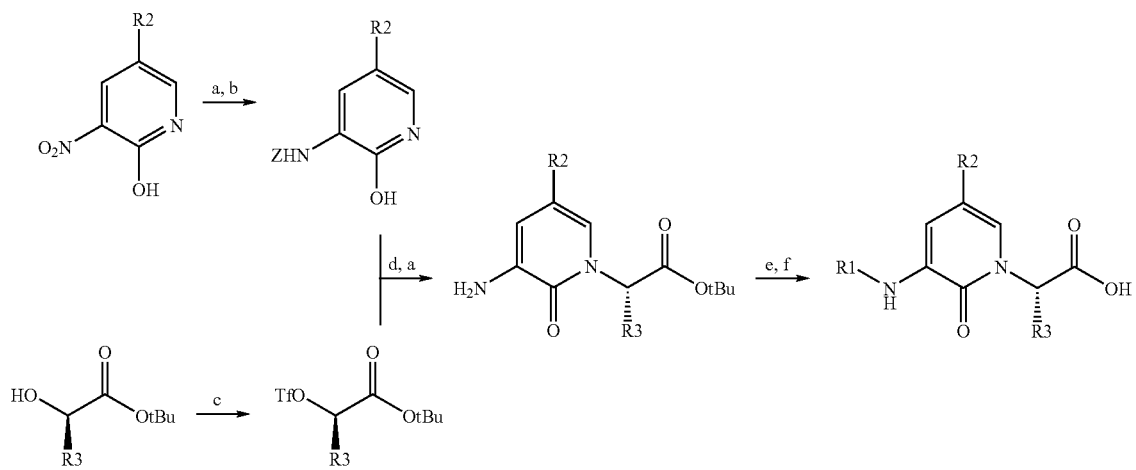

Scheme III
(a) $H_2$ Pd/C MeOH;
(b) $PhCH_2O$ (CO) Cl/$Na_2CO_3$/$H_2O$/THF;
(c) $(CF_3SO_2)_2O$/ 2, 6-Lutidine/DCM;
(d) NaH/THF;
(e) R1-Cl/$Et_3N$/DMAP/DCM;
(f) TFA/DCM In Scheme III the following abbreviations are used: Z is a benzyloxycarbonyl protecting group; MeOH is methanol; DCM is dichloromethane; TFA is trifluoroacetic acid; DMAP is 4-dimethylaminopyridine; THF is tetrahydrofuran. Pyridone acid derivatives I can be prepared in chiral form using the synthetic sequence shown in Scheme III. The starting (2-oxo-1,2-dihydro-pyridin-3-yl)-carbamic acid benzyl ester ($R^2$=H) is prepared using a procedure similar to that described by Warner et al *J. Med. Chem.* 1994, 37(19), 3090-3099 Commercially available (R)-tert-butyl-2-hydroxybutyrate ($R^3$=ethyl) is treated with trifluoromethanesulphonic anhydride and 2,6-lutidine in DCM to give the corresponding triflate. Reaction of the triflate with the anion of (2-oxo-1,2-dihydro-pyridin-3-yl)-carbamic acid benzyl ester (prepared by deprotonation with sodium hydride in THF) gives the N-alkylated pyridone. Removal of the benzyloxycarbonyl protecting group using hydrogen and palladium on carbon gives the amine. This is then reacted with an appropriate electrophile, triethylamine and DMAP in DCM. For example if $R^1$ is required to be RC=O (an amide) then an appropriately substituted acid chloride may be used. If $R^1$ is required to be RS(=O)$_2$ (sulphonamide) then an appropriately substituted sulfonyl chloride may be used. If $R^1$ is RO(C=O) (carbamate) then an appropriately substituted chloroformate may be used. If $R^1$ is RN(C=O) (urea) then an appropriately substituted carbamoyl chloride or isocyanate may be used. The other $R^1$ groups may be prepared accordingly. Acid 1 is then prepared by deprotection of the ester by, for example, using trifluoroacetic acid. The acid is then coupled to amino alcohol 2 (Scheme 1).

wherein $R^1$, $R^2$, $R^3$, $R^4$, and $R^5$, are as defined in any of the embodiments herein, comprising:
(a) reacting a compound of formula (III):

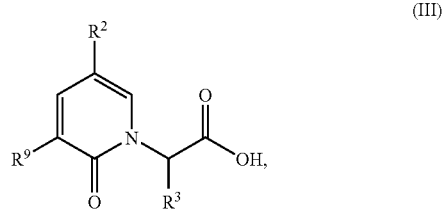

(III)

wherein:
$R^9$ is —$NO_2$, —C(O)O$R^{10}$, $^6$C(O)N(H)—, $R^6SO_2N(H)$—, $R^6OC(O)N(H)$—, $(R^6)_2NC(O)N(H)$—, $R^6C(O)C(O)N(H)$—, $R^6N(H)$—, $(R^6)_2NC(O)C(O)N(H)$—, or $R^6OC(O)C(O)N(H)$—;
$R^{10}$ is independently hydrogen, (C1-C12)-aliphatic-(C3-C10)-cycloaliphatic-, (C6-C10)-aryl-, (C3-C10)-heterocyclyl-, (C5-C10)-heteroaryl-, (C3-C10)-cycloaliphatic-(C1-C12)-aliphatic-, (C6-C10)-aryl-(C1-C12)-aliphatic-, (C3-C10)-heterocyclyl-(C1-C12)-aliphatic-, (C5-C10)-heteroaryl(C1-C12)-aliphatic-, wherein up to 3 aliphatic carbon atoms may be replaced with a group selected from O, N(H), N(R), S, SO, and SO$_2$; and wherein $R^{10}$ is optionally substituted with up to 6 substituents independently selected from R; and R, $R^2$, $R^3$, and $R^6$ are as defined in any of the embodiments of formula (I) herein;
with a compound of formula (IV):

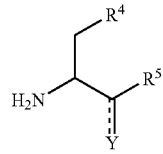

(IV)

wherein Y is either a carbonyl group or an OH group; and $R^4$ and $R^5$ are as defined in any of the embodiments of formula (I) herein;
in the presence of peptide coupling conditions and a solvent;
provided that if Y is an OH group, then the process further comprises (b) oxidizing the OH group to provide the compound of formula (I); and
provided that if $R^9$ is —$NO_2$, —C(O)$OR^{10}$, or —CN, the process comprises the further step of converting the —$NO_2$, —C(O)$OR^{10}$, or —CN into $R^6$C(O)N(H)—, $R^6SO_2$N(H)—, $R^6$OC(O)N(H)—, $(R^6)_2$NC(O)N(H)—, $R^6$C(O)C(O)N(H)—, $R^6$N(H)—, $(R^6)_2$NC(O)C(O)N(H)—, or $R^6$C(O)C(O)N(H)—.

The coupling conditions may be any known to skilled practitioners for forming peptidyl bonds. Preferred coupling conditions are EDC/DMAP/HOBt. A preferred solvent in the above embodiment is THF.

In a preferred embodiment, the compound of formula (III):

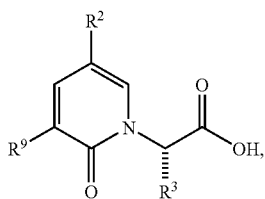

(III)

wherein $R^2$, $R^3$, and $R^9$ are as defined herein; is prepared by a process comprising:
(c) reacting a compound of formula (V):

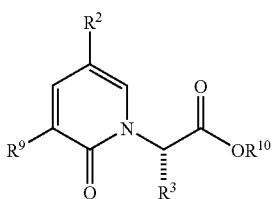

(V)

wherein R, $R^2$, $R^3$, and $R^9$ are as defined herein; in a solvent in the presence of deprotecting conditions.

The deprotecting conditions will depend on the specific protecting group (i.e., $R^{10}$). For example, if $R^{10}$ is t-butyl, then preferred deprotecting conditions would include acid hydrolysis. A preferred acid is TFA. A preferred solvent is DCM. More preferably the solvent and the hydrolyzing conditions comprise TFA and DCM. If $R^{10}$ is methyl or ethyl, then preferred deprotecting conditions would be basic (e.g., aqueous NaOH). If $R^{10}$ is benzyl, then the benzyl group could be removed by hydrogenolysis.

In a preferred embodiment, the compound of formula (V):

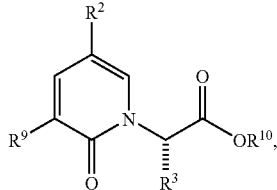

(V)

wherein $R^2$, $R^3$, $R^9$, and $R^{10}$ are as defined herein;
is prepared by a process comprising:
(d) reacting a compound of formula (VI):

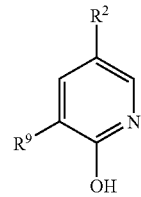

(VI)

wherein $R^2$ and $R^9$ are as defined herein;
with a compound of formula (VII):

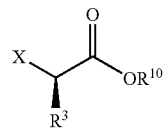

(VII)

wherein X is a suitable leaving group; and
$R^3$ and $R^{10}$ are as defined herein;
in the presence of a solvent and a base.

Preferably, X is —I, —Br, —Cl, —OH, an alkylsulfonate, or an aryl sulfonate. When X is —OH, an appropriate leaving group may be generated in situ (e.g., as in the Mitsunobu reaction). Preferred sulfonates include —O-trifluoromethanesulfonate, —O-methanesulfonate, —O-benzenesulfonate, —O-p-toluenesulfonate, —O-m-nitrobenzenesulfonate, and —O-p-nitrobenzenesulfonate. Suitable leaving groups useful in the methods of this invention are well known in the art. See, e.g., "March's Advanced Organic Chemistry", 5th Ed., Ed.: Smith, M. B. and March, J., John Wiley & Sons, New York (2001).

Any solvent that is compatible with the generation of anions may be used. Preferred solvents include DMF, toluene, and THF.

Suitable bases include any that may remove a proton from the hydroxy group in (V). Such bases include BuLi, LDA, LHMDS, and NaH. Preferably, the base is NaH.

Another embodiment of this invention provides a process for preparing a compound of formula (VIII):

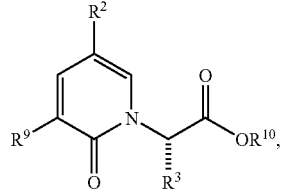

(VIII)

wherein:
$R^2$ is —$CF_3$, —Cl, —$OR^7$, —$NO_2$, —$OCF_3$, —CN, or $R^8$; and
$R^3$, $R^8$, $R^9$, and $R^{10}$ are as defined herein;

comprising the step of (e) reacting a compound of formula (IX):

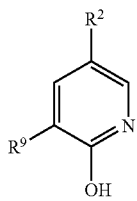

wherein $R^2$ and $R^9$ are as defined herein;
with a compound of formula (VII):

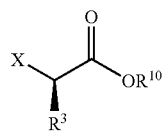

wherein $R^3$ and $R^{10}$ are as defined herein; and
X is a suitable leaving group;
in the presence of a solvent and a base.

Preferably, X is —I, —Br, —Cl, —OH, an alkylsulfonate, or an aryl sulfonate. When X is —OH, an appropriate leaving group may be generated in situ (e.g., as in the Mitsunobu reaction). Preferred sulfonates include —O-trifluoromethanesulfonate, —O-methanesulfonate, —O-benzenesulfonate, —O-p-toluenesulfonate, —O-m-nitrobenzenesulfonate, and —O-p-nitrobenzenesulfonate.

Any solvent is compatible with the generation of anions may be used. Such solvents include DMF, toluene, and THF. Preferably, the solvent is THF.

Suitable bases include any that may remove a proton from the hydroxy group in (V). Such bases include BuLi, LDA, LHMDS, and NaH. Preferably, the base is NaH.

Another embodiment of this invention provides a process for preparing a compound of formula (I):

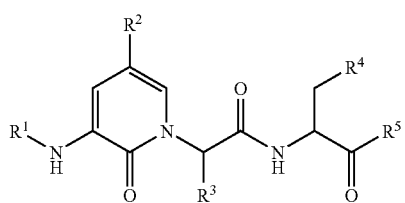

wherein $R^1$, $R^2$, $R^3$, $R^4$, and $R^5$, are as defined in any of the embodiments herein, comprising:
(a) reacting a compound of formula (VI or IX):

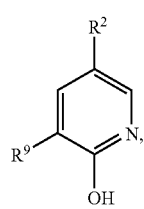

wherein:
$R^9$ is —$NO_2$, —$C(O)OR^{10}$, —CN, $R^6C(O)N(H)$—, $R^6SO_2N(H)$—, $R^6OC(O)N(H)$—, $(R^6)_2NC(O)N(H)$—, $R^6C(O)C(O)N(H)$—, $R^6N(H)$—, $(R^6)_2NC(O)C(O)N(H)$—, or $R^6OC(O)C(O)N(H)$—; and
$R^2$, $R^3$ and $R^6$ are as defined herein;

with a compound of formula (X):

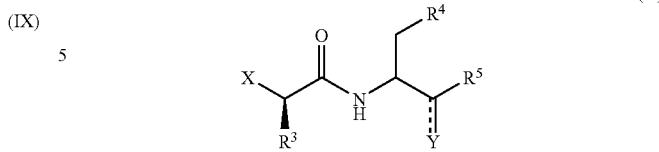

wherein Y is either a carbonyl group or an OH group; and
$R^4$ and $R^5$ are as defined herein;
in the presence of any of the coupling conditions defined herein and a solvent;
provided that if Y is an OH group, then the process further comprises (b) oxidizing the OH group to provide the compound of formula (I); and
provided that if $R^9$ is —$NO_2$, —$C(O)OR^{10}$, or —CN, the process comprises the further step of converting the —$NO_2$, —$C(O)OR^{10}$, or —CN into $R^6C(O)N(H)$—, $R^6SO_2N(H)$—, $R^6OC(O)N(H)$—, $(R^6)_2NC(O)N(H)$—, $R^6C(O)C(O)N(H)$—, $R^6N(H)$—, $(R^6)_2NC(O)C(O)N(H)$—, or $R^6OC(O)C(O)N(H)$—.

The compounds of this invention can be assayed for their ability to inhibit the release of IL-1β caspase activity, or apoptosis directly. Assays for each of the activities are known in the art. Selected assays are described below.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The above-described compositions are particularly useful in therapeutic applications relating to an IL-1 mediated disease, an apoptosis mediated disease, an inflammatory disease, an autoimmune disease, a destructive bone disorder, a proliferative disorder, an infectious disease, a degenerative disease, a disease associated with cell death, or various forms of liver disease. Such diseases include those related to rheumatology and autoimmunity, such as rheumatoid arthritis, osteoarthritis, osteoporosis, systemic lupus erythematosus, scleroderma, chronic thyroiditis, Grave's disease, myasthenia gravis, autoimmune neutropenia, autoimmune hemolytic anemia, thrombocytopenia, juvenile rheumatoid arthritis, gout, Behcet's syndrome, Still's syndrome, macrophage activation syndrome, and sarcoidosis; auto-inflammatory syndromes, such as cryopyrin-associated Periodic Syndromes, (including Muckle-Wells syndrome, familial cold urticaria, chronic infantile neurological cutaneous and articular syndrome (a.k.a. neonatal onset multisystem inflammatory disease)), familial Mediterranean fever, TNFR1-Associated Periodic Syndrome (TRAPS), Hyper-IgD periodic fever Syndrome (HIDS), and Blau's syndrome; dermatology, such as psoriasis, atopic dermatitis, scarring, alopecia, acne vulgaris, and pemphigus; respiratory, such as asthma, adult respiratory distress syndrome, cystic fibrosis, emphysema, chronic bronchitis, chronic obstructive pulmonary disease, and idiopathic pulmonary fibrosis; internal medicine, such as inflammatory peritonitis, inflammatory bowel disease, Crohn's disease, ulcerative colitis, autoimmune gastritis, *H. pylori*-associated gastric and duodenal ulcer disease, diabetes, pancreatitis, glomerulonephritis, chronic active hepatitis, excess dietary alcohol intake disease, renal disease, polycystic kidney disease, burns, organ apoptosis after burn injury, haemorrhagic shock, organ failure (e.g., hepatic failure, acute renal failure, and acute respiratory failure), and endometriosis; transplants, such as graft vs. host disease (GVHD) and organ transplant rejection; oncology, such as leukemias and related disorders, myelodysplastic syndrome, multiple myeloma-related bone disorder, acute myelogenous leukemia, chronic myelogenous leukemia, metastatic melanoma, Kaposi's sarcoma, and multiple myeloma; cardiovascular, such as chronic heart disease, acute heart disease, myocardial infarction, myocardial ischemia, congestive heart failure, atherosclerosis, coronary artery bypass graft (CABG), and acute coronary syndrome; the central and peripheral nervous systems, such as Alzheimer's disease, Parkinson's disease, Huntington's disease, Kennedy's disease, prion disease, cerebral ischemia, epilepsy, spinal muscular atrophy, amyotrophic lateral sclerosis, multiple sclerosis, HIV-related encephalitis, traumatic brain injury, spinal cord injury, neurological damage due to stroke, diabetic neuropathy, and acute and chronic pain; ophthalomology, such as uveitis, retinal disorders, diabetic retinopathy, glaucoma, and keratitis; infectious diseases, such as viral mediated disease, sepsis, septic shock, Shigellosis, hepatitis-B, hepatitis-C, hepatitis-G, yellow fever, dengue fever, Japanese encephalitis, HIV infection, tuberculosis, meningitis, *Pseudomonas* infection, and *Acinetobacter* infection; and other diseases, such as aging. The compounds and compositions are also useful in treating complications associated with coronary artery bypass grafts. The amount of compound present in the above-described compositions should be sufficient to cause a detectable decrease in the severity of the disease or in caspase activity and/or cell apoptosis, as measured by any of the assays known in the art.

According to another embodiment, the compositions of this invention may further comprise another therapeutic agent. Such agents include, but are not limited to, thrombolytic agents such as tissue plasminogen activator and streptokinase. When a second agent is used, the second agent may be administered either as a separate dosage form or as part of a single dosage form with the compounds or compositions of this invention. Accordingly, a combined preparation for simultaneous, separate, or sequential use is provided by this invention.

Dosage levels of between about 0.01 and about 100 mg/kg body weight per day, preferably between about 0.5 and about 75 mg/kg body weight per day of the protease inhibitor compounds described herein are useful in a monotherapy for the prevention and treatment of a disease involving caspase activity and/or apoptosis.

Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula I and one or more additional therapeutic or prophylactic agents, both the compound and the additional agent should be present at dosage levels of between about 10 to 100%, and more preferably between about 10 to 80% of the dosage normally administered in a monotherapy regimen.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and other therapeutic agent, if present, in the composition.

In a preferred embodiment, the invention provides a method of treating a mammal, having one of the aforementioned diseases, comprising the step of administering to said mammal a pharmaceutically acceptable composition described above. In this embodiment, if the patient is also administered another therapeutic agent or caspase inhibitor, it may be delivered together with the compound of this invention in a single dosage form, or, as a separate dosage form. When administered as a separate dosage form, the other caspase inhibitor or agent may be administered prior to, at the same time as, or following administration of a pharmaceutically acceptable composition comprising a compound of this invention.

In order that this invention be more fully understood, the following preparative and testing examples are set forth. These examples are for the purpose of illustration only and are not to be construed as limiting the scope of the invention in any way.

Example 1

(S,S)-3-[2-(3-Acetylamino-2-oxo-2H-pyridin-1-yl)-butyrylamino]-4-oxo-5-(2,3,5,6-tetrafluoro-phenoxy)-pentanoic acid

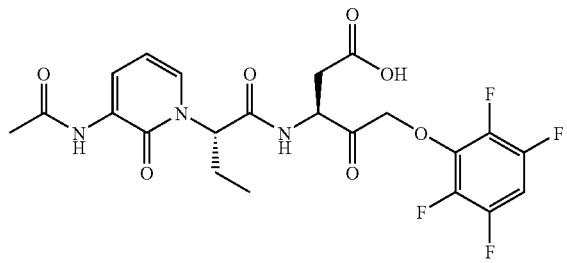

Method A:

(S)-2-(3-Benzyloxycarbonylamino-2-oxo-2H-pyridin-1-yl)-butyric acid tert-butyl ester

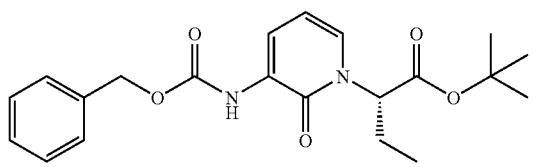

To a cooled (0° C.) solution of (R)-tert-butyl hydroxybutyrate (1.03 g, 6.43 mmol) in dichloromethane (25 mL), was slowly added 2,6-lutidine (1.38 g, 12.9 mmol) and then trifluoromethanesulfonic anhydride (3.45 g, 12.2 mmol). The resulting mixture was stirred at 0° C. for 1 hour, then partitioned between tert-butylmethyl ether (150 mL) and an aqueous solution of 1M HCl (30 mL). The organic layer was washed with brine (30 mL), dried (sodium sulfate), filtered and concentrated to afford the triflate as a light brown oil.

To a solution of (2-oxo-1,2-dihydro-pyridin-3-yl)-carbamic acid benzyl ester (P. Warner et al., *J. Med. Chem.*, 37, 19, 1994, 3090-3099)(1.73 g, 7.07 mmol) in dry THF (60 mL) was added sodium hydride (60% dispersion, 257 mg, 6.43 mmol) and the solution was stirred at room temperature for 45 minutes. The reaction mixture was then slowly transferred with a canula onto a solution of the triflate prepared above in THF (3 mL). The reaction mixture was stirred at room temperature for 90 minutes and quenched with aqueous ammonium chloride (10 mL). Most of the solvent was evaporated and the residue was partitioned between EtOAc and saturated aqueous NH$_4$Cl. The organic layer was washed with brine (30 mL), dried (MgSO$_4$), filtered and evaporated. The residue was purified by flash chromatography (10% ethyl acetate/hexane) to afford the title compound as a colourless oil (2.48 g, 100%): $^1$H NMR (400 MHz, CDCl$_3$) δ 0.92 (3H, t), 1.45 (9H, s), 1.94 (1H, m), 2.25 (1H, m), 5.23 (2H, s), 5.47 (1H, dd), 6.32 (1H, t), 7.01 (1H, d), 7.32-7.43 (5H, m), 7.92 (1H, s), 8.06 (1H, br d)

Method B:

(S)-2-(3-Amino-2-oxo-2H-pyridin-1-yl)-butyric acid tert-butyl ester

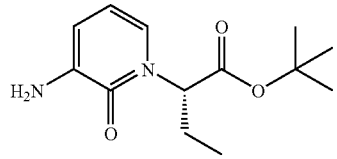

To a solution of (S)-2-(3-Benzyloxycarbonylamino-2-oxo-2H-pyridin-1-yl)-butyric acid tert-butyl ester (2.48 g, 6.43 mmol) in a mixture of MeOH (15 mL) and EtOAc (15 mL) was added 10% Pd/C (250 mg). The mixture was degassed and stirred at room temperature for 90 minutes under an atmosphere of hydrogen (balloon pressure). The reaction mixture was filtered through a short pad of silica which was then flushed with MeOH. The combined filtrates were evaporated under reduced pressure to afford the title compound as a white solid (1.62 g, 100%); $^1$H NMR (400 MHz, CDCl$_3$) δ 0.91 (3H, t), 1.44 (9H, s), 1.91 (1H, m), 2.21 (1H, m), 4.24 (2H, br s), 5.50 (1H, dd), 6.11 (1H, t), 6.53 (1H, d), 6.77 (1H, d)

Method C:

(S)-2-(3-Acetylamino-2-oxo-2H-pyridin-1-yl)-butyric acid tert-butyl ester

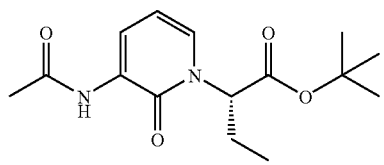

To a cooled (0° C.) solution of (S)-2-(3-Amino-2-oxo-2H-pyridin-1-yl)-butyric acid tert-butyl ester (500 mg, 1.98 mmol) in dichloromethane (5 mL) was added triethylamine (220 mg, 2.18 mmol) followed by acetic anhydride (202 mg, 1.98 mmol). The reaction mixture was stirred at room temperature for 12 hours and then partitioned between EtOAc and aqueous 1M HCl. The organic layer was washed with saturated aqueous NaHCO$_3$, brine (30 mL), dried (MgSO$_4$), filtered and evaporated. The residue was purified by flash chromatography (40% ethyl acetate/hexane) to afford the title compound as a colourless oil (569 mg, 97%): $^1$H NMR (400 MHz, CDCl$_3$) δ 0.87 (3H, t), 1.40 (9H, s), 1.91 (1H, m), 2.13 (3H, s), 2.19 (1H, m), 5.38 (1H, dd), 6.26 (1H, t), 6.99 (1H, d), 8.33 (1H, d), 8.43 (1H, br s).

Method D:

(S)-2-(3-Acetylamino-2-oxo-2H-pyridin-1-yl)-butyric acid

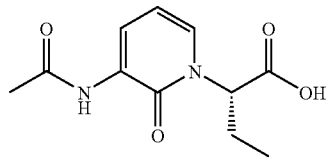

A solution of (S)-2-(3-Acetylamino-2-oxo-2H-pyridin-1-yl)-butyric acid tert-butyl ester (569 mg, 1.93 mmol) in dichloromethane (5 mL) was cooled to 0° C. Trifluoroacetic acid (5 ml) was added and the resulting mixture allowed to warm to room temperature and stir for 2 hours. The mixture was then concentrated under reduced pressure and the residue redissolved in dichloromethane. This process was repeated several times in order to remove excess trifluoroacetic acid. The resulting solid was slurried in diethyl ether, filtered and washed with more diethyl ether. The solid was then dried to constant weight under vacuum. This gave the title product as a white solid (327 mg, 71%); $^1$H NMR (400 MHz, d6-DMSO) δ 0.78 (3H, t), 2.02-2.17 (5H, m), 4.98 (1H, dd), 6.29 (1H, t), 7.35 (1H, d), 8.21 (1H, d), 9.30 (1H, s), 13.07 (1H, vbr s).

Method E:

(S,S)-3-[2-(3-Acetylamino-2-oxo-2H-pyridin-1-yl)-butyrylamino]-4-hydroxy-5-(2,3,5,6-tetrafluoro-phenoxy)-pentanoic acid tert-butyl ester

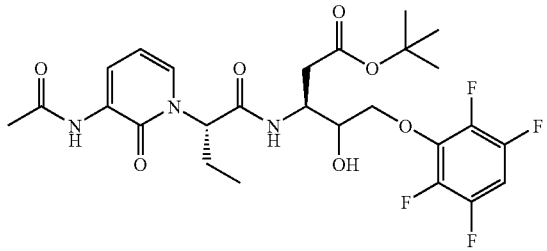

A stirred mixture of (S)-2-(3-Acetylamino-2-oxo-2H-pyridin-1-yl)-butyric acid (100 mg, 0.42 mmol), 3-amino-5-(2,3,5,6-tetrafluorophenoxy)-4-hydroxy-pentanoic acid tert-butyl ester (163 mg, 0.462 mmol), HOBt (62 mg, 0.462 mmol), DMAP (56 mg, 0.462 mmol) and THF (5 mL) was cooled to 0° C. then EDC (89 mg, 0.462 mmol) was added. The mixture was allowed to warm to room temperature during 16 h then concentrated under reduced pressure. The residue was purified by flash chromatography (50-50% ethyl acetate/hexane) to afford the title compound as a white foam (221 mg, 92%);

¹H NMR (400 MHz, CDCl₃) δ 0.88-0.93 (3H, m), 1.37-1.38 (9H, 2 s), 1.86-1.96 (1H, m), 2.15-2.25 (4H, m), 2.55-2.71 (2H, m), 3.70-4.64 (5H, m), 5.30-5.39 (1H, m), 6.30-6.35 (1H, m), 6.75-6.86 (1H, m), 7.17-7.31 (2H, m), 8.31-8.47 (2H, m).

Method F:

(S,S)-3-[2-(3-Acetylamino-2-oxo-2H-pyridin-1-yl)-butyrylamino]-4-oxo-5-(2,3,5,6-tetrafluoro-phenoxy)-pentanoic acid tert-butyl ester

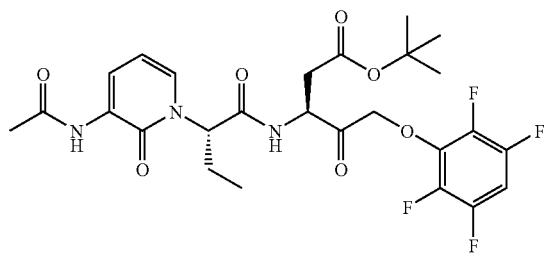

A stirred solution of (S,S)-3-[2-(3-Acetylamino-2-oxo-2H-pyridin-1-yl)-butyrylamino]-4-hydroxy-5-(2,3,5,6-tetrafluoro-phenoxy)-pentanoic acid tert-butyl ester (221 mg, 0.385 mmol) in anhydrous DCM (10 mL) was treated with 1,1,1-triacetoxy-1,1-dihydro-1,2-benziodoxol-3(1H)-one (212 mg, 0.5 mmol) at 0° C. The resulting mixture was kept at 0° C. for 2 hr, diluted with ethyl acetate, then poured into a 1:1 mixture of saturated aqueous sodium hydrogen carbonate and saturated aqueous sodium thiosulfate. The organic layer was removed and the aqueous layer re-extracted with ethyl acetate. The combined organic extracts were dried (Magnesium sulfate) and concentrated. The residue was purified by flash chromatography (50-50% ethyl acetate/hexane) to afford the title compound as a white solid (187 mg, 85%); ¹H NMR (400 MHz, CDCl₃) δ 0.93 (3H, t), 1.36 (3H, s), 1.95 (1H, m), 2.21 (3H, s), 2.25 (1H, m), 2.73 (2H, dd), 2.89 (1H, dd), 4.91 (1H, m), 5.04-5.17 (2H, m), 5.47 (1H, m), 6.34 (1H, t), 6.80 (1H, m), 7.19 (1H, m), 7.68 (1H, d), 8.36-8.41 (2H, m).

Method G:

(S,S)-3-[2-(3-Acetylamino-2-oxo-2H-pyridin-1-yl)-butyrylamino]-4-oxo-5-(2,3,5,6-tetrafluoro-phenoxy)-pentanoic acid

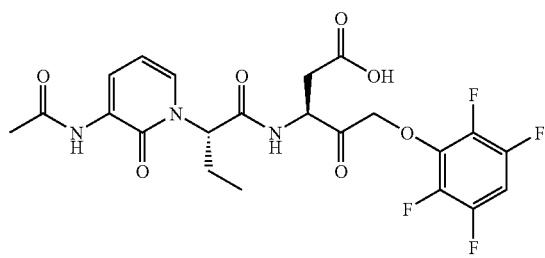

A solution of (S,S)-3-[2-(3-Acetylamino-2-oxo-2H-pyridin-1-yl)-butyrylamino]-4-oxo-5-(2,3,5,6-tetrafluoro-phenoxy)-pentanoic acid tert-butyl ester (187 mg, 0.327 mmol) in dichloromethane (5 mL) was cooled to 0° C. Trifluoroacetic acid (5 ml) was added and the resulting mixture allowed to warm to room temperature and stir for 2 hours. The mixture was then concentrated under reduced pressure and the residue redissolved in dichloromethane. This process was repeated several times in order to remove excess trifluoroacetic acid. The resulting solid was slurried in diethyl ether, filtered and washed with more diethyl ether. The solid was then dried to constant weight under vacuum. This gave the title product as a white solid (138 mg, 82%); ¹H NMR (400 MHz, d6-DMSO) δ 0.78 (3H, t), 1.87-2.13 (5H, m), 2.56-2.78 (2H, m), 4.62 (1H, m), 5.18-5.29 (2H, m), 5.40 (1H, m), 6.28 (1H, t), 7.37 (1H, d), 7.53-7.66 (1H, m), 8.17-8.21 (1H, m), 8.92 (1H, d), 9.21 (1H, s), 12.51 (1H, br s); ¹⁹F NMR (376 MHz, d6-DMSO, proton-decoupled) δ –156.9, –141.1; M+H 516.2, M–H 514.2.

Example 2

(S,S)-4-Oxo-3-[2-(2-oxo-3-propionylamino-2H-pyridin-1-yl)-butyrylamino]-5-(2,3,5,6-tetrafluoro-phenoxy)-pentanoic acid

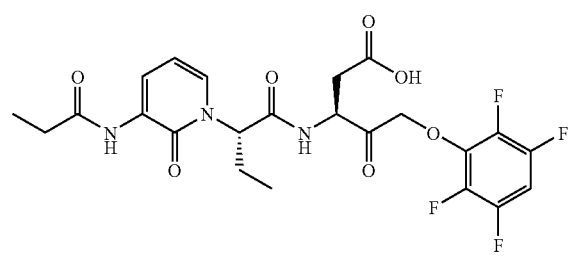

Prepared from (S)-2-(3-Amino-2-oxo-2H-pyridin-1-yl)-butyric acid tert-butyl ester and propionic anhydride according to methods C-G; white solid; IR (solid) 1584, 1642, 1662, 1717, 1749 cm–1; ¹H NMR (400 MHz, d6-DMSO) δ 0.78 (3H, t), 1.04 (3H, t), 1.88-2.11 (2H, m), 2.43 (2H, q), 2.59 (1H, d), 2.75 (1H, dd), 4.61 (1H, m), 5.18-5.29 (2H, 2 dd), 5.40 (1H, m), 6.29 (1H, t), 7.37 (1H, d), 7.58 (1H, m), 8.22 (1H, d), 8.91 (1H, d), 9.08 (1H, s), 12.50 (1H, br s); ¹⁹F NMR (376 MHz, d6-DMSO, proton-decoupled) δ –140.6, –140.8, –141.1, –156.8, –157.0; M+H 530.2, M–H 528.3.

Example 3

(S,S)-3-[2-(3-Butyrylamino-2-oxo-2H-pyridin-1-yl)-butyrylamino]-4-oxo-5-(2,3,5,6-tetrafluoro-phenoxy)-pentanoic acid

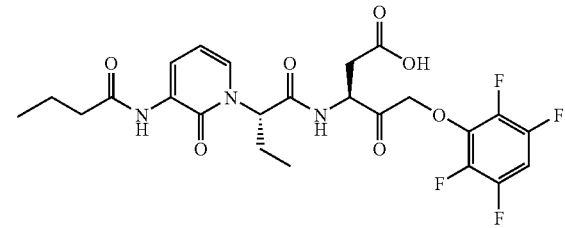

Prepared from (S)-2-(3-Amino-2-oxo-2H-pyridin-1-yl)-butyric acid tert-butyl ester and butyryl chloride according to methods C-G; beige solid; IR (solid) 1659, 1645, 1509, 1490 cm–¹; ¹H NMR (400 MHz, d6-DMSO) δ 0.76-0.80 (3H, m), 0.88 (3H, t), 1.53-1.58 (2H, m), 1.88-1.93 (1H, m), 2.01-2.09 (1H, m), 2.37-2.41 (2H, m), 2.59 (1H, dd), 2.70-2.81 (1H, m), 4.59-4.63 (1H, m), 5.20-5.25 (2H, m), 5.38-5.50 (1H, 2×m), 7.36-7.38 (1H, m), 7.55-7.61 (1H, m), 8.21-8.23 (1H, m), 8.61-8.92 (1H, 3×d), 9.06-9.10 (1H, m), 12.49 (1H, br s); $^{19}$F NMR (376 MHz, d6-DMSO, proton-decoupled) δ −140.6, −141.1, −156.9, −157.0; M+H 544.3, M−H 542.3.

Example 4

(S,S)-3-{2-[3-(Cyclopropanecarbonyl-amino)-2-oxo-2H-pyridin-1-yl]-butyrylamino}-4-oxo-5-(2,3,5,6-tetrafluoro-phenoxy)-pentanoic acid

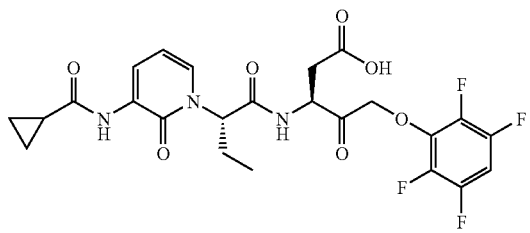

Prepared from (S)-2-(3-Amino-2-oxo-2H-pyridin-1-yl)-butyric acid tert-butyl ester and cyclopropanecarbonyl chloride according to methods C-G; white solid; $^1$H NMR (400 MHz, d6-DMSO) δ 0.74-0.82 (7H, m), 1.93 (1H, m), 2.07 (1H, m), 2.17 (1H, m), 2.59 (1H, d), 2.75 (1H, dd), 4.62 (1H, m), 5.19-5.30 (2H, 2 dd), 5.41 (1H, m), 6.27 (1H, t), 7.37 (1H, d), 7.57 (1H, m), 8.17 (1H, d), 8.92 (1H, d), 9.49 (1H, s), 12.51 (1H, br s); M+H 542.2, M−H 540.3.

Example 5

(S,S)-3-[2-(3-Isobutyrylamino-2-oxo-2H-pyridin-1-yl)-butyrylamino]-4-oxo-5-(2,3,5,6-tetrafluoro-phenoxy)-pentanoic acid

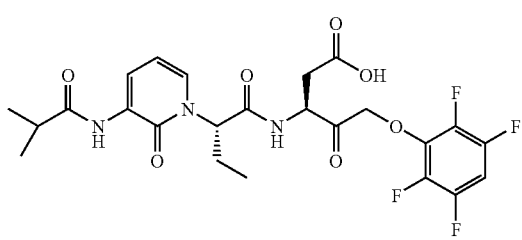

Prepared from (S)-2-(3-Amino-2-oxo-2H-pyridin-1-yl)-butyric acid tert-butyl ester and isobutyryl chloride according to methods C-G; white solid; IR (solid) 1664, 1517, 1491 cm−$^1$; $^1$H NMR (400 MHz, d6-DMSO) δ 1.75-1.85 (3H, m), 1.05 (6H, d), 1.9-2.1 (2H, m), 2.6-2.9 (3H, m), 4.55-4.62 (1H, m), 5.2-5.35 (2H, m), 5.4-5.43 (1H, m), 6.25 (1H, t), 7.4-7.45 (1H, m), 7.6-7.7 (1H, m), 8.2-8.24 (1H, m), 8.8-9.0 (2H, m); M+H 544.3, M−H 542.3.

Example 6

(S,S)-3-{2-[3-(2-Methoxy-acetylamino)-2-oxo-2H-pyridin-1-yl]-butyrylamino}-4-oxo-5-(2,3,5,6-tetrafluoro-phenoxy)-pentanoic acid

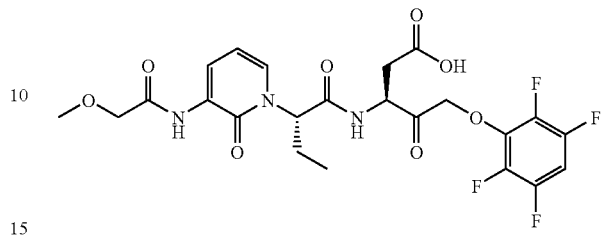

Prepared from (S)-2-(3-Amino-2-oxo-2H-pyridin-1-yl)-butyric acid tert-butyl ester and methoxyacetyl chloride according to methods C-G; pink solid; $^1$H NMR (400 MHz, d6-DMSO) δ 0.75-0.80 (3H, m), 1.88-1.97 (1H, m), 2.02-2.10 (1H, m), 2.56-2.63 (1H, m), 2.72-2.79 (1H, m), 3.37-3.40 (3H, m), 4.00-4.03 (2H, m), 4.53-4.65 (1H, m), 5.13-5.46 (3H, m), 6.32-6.35 (1H, m), 7.39-7.45 (1H, m), 7.51-7.66 (1H, m), 8.21-8.26 (1H, m), 8.92-8.98 (1H, m), 9.12-9.17 (1H, m), 12.51 (1H, br s); M+H 546.2, M−H 544.2.

Example 7

(S,S)-3-(2-{3-[(Furan-2-carbonyl)-amino]-2-oxo-2H-pyridin-1-yl}-butyrylamino)-4-oxo-5-(2,3,5,6-tetrafluoro-phenoxy)-pentanoic acid

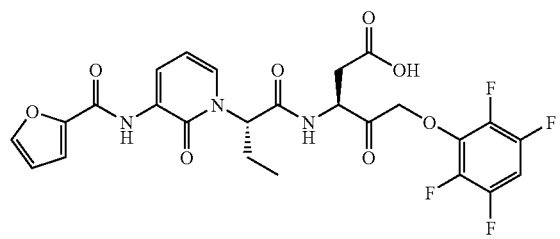

Prepared from (S)-2-(3-Amino-2-oxo-2H-pyridin-1-yl)-butyric acid tert-butyl ester and 2-furoyl chloride according to methods C-G; white solid; $^1$H NMR (400 MHz, d6-DMSO) δ 0.81 (3H, m), 1.95 (1H, m), 2.09 (1H, m), 2.60 (1H, dd), 2.77 (1H, dd), 4.61 (1H, m), 5.19-5.29 (2H, m), 5.42 (1H, m), 6.39 (1H, t), 6.74 (1H, m), 7.30 (1H, m), 7.46-7.58 (2H, m), 7.95 (1H, m), 8.27 (1H, d), 8.98 (1 Hd), 9.16 (1H, s), 12.50 (1H, br s); M+H 568.3, M−H 566.3.

Example 8

(S,S)-3-(2-{3-[(Furan-3-carbonyl)-amino]-2-oxo-2H-pyridin-1-yl}-butyrylamino)-4-oxo-5-(2,3,5,6-tetrafluoro-phenoxy)-pentanoic acid

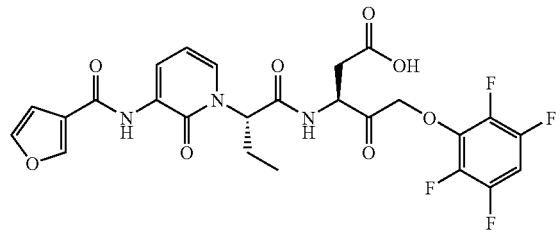

Prepared from (S)-2-(3-Amino-2-oxo-2H-pyridin-1-yl)-butyric acid tert-butyl ester and 3-furoyl chloride according to methods C-G; off-white solid; IR (solid) 1748, 1711, 1663, 1640, 1583, 1517, 1488 cm−1; 1H NMR (400 MHz, d6-DMSO) δ 0.80 (3H, m), 1.90-2.20 (2H, m), 2.60-2.90 (2H, m), 4.65 (1H, m), 5.10-5.60 (3H, m), 6.40 (1H, t), 6.95 (1H, m), 7.40-7.65 (2H, m), 7.85 (1H, s), 8.20 (1H, m), 8.50 (1H, m), 8.90-9.20 (2H, m); 19F NMR (376 MHz, d6-DMSO, proton-decoupled) δ −141.0, −156.8; M+H 568.2, M−H 566.3.

Example 9

(S,S)-4-Oxo-3-(2-{2-oxo-3-[(pyridine-3-carbonyl)-amino]-2H-pyridin-1-yl}-butyrylamino)-5-(2,3,5,6-tetrafluoro-phenoxy)-pentanoic acid

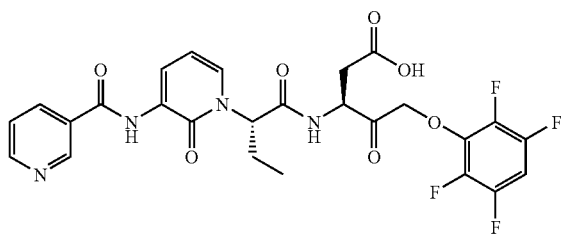

Prepared from (S)-2-(3-Amino-2-oxo-2H-pyridin-1-yl)-butyric acid tert-butyl ester and 3-pyridinecarbonyl chloride according to methods C-G (isolated as a TFA salt); yellow solid; IR (solid) 1745, 1678, 1650, 1517, 1488; 1H NMR (400 MHz, d6-DMSO) δ 0.80 (3H, m), 1.90-2.30 (2H, m), 2.50-2.90 (2H, m), 4.65 (1H, m), 5.10-5.65 (3H, m), 6.45 (1H, t), 7.40-7.80 (3H, m), 8.10-8.40 (2H, m), 8.85 (1H, s), 8.90-9.20 (2H, m), 9.65 (1H, m); 19F NMR (376 MHz, d6-DMSO, proton-decoupled) δ −141.0, −156.8; M+H 579.2, M−H 577.3.

Example 10

(S,S)-3-(2-{3-[(Isothiazole-3-carbonyl)-amino]-2-oxo-2H-pyridin-1-yl}-butyrylamino)-4-oxo-5-(2,3,5,6-tetrafluorophenoxy)-pentanoic acid

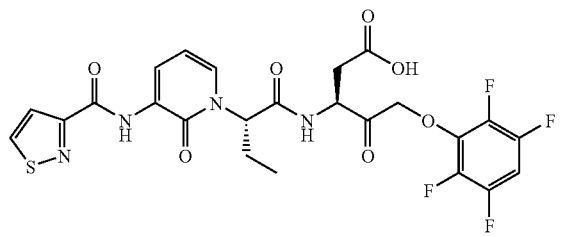

Prepared from (S)-2-(3-Amino-2-oxo-2H-pyridin-1-yl)-butyric acid tert-butyl ester and 3-isothiazolecarbonyl chloride according to methods C-G; pink solid; IR (solid) 1678, 1649, 1516, 1493 cm−1; 1H NMR (400 MHz, d6-DMSO) δ 0.85 (3H, m), 1.85-2.30 (2H, m), 2.50-2.90 (2H, m), 4.20-4.70 (1H, 2 m), 5.10-5.60 (3H, m), 6.45 (1H, t), 7.40-7.70 (2H, m), 7.95 (1H, m), 8.40 (1H, d), 8.95-9.15 (1H, 2 m), 9.30 (1H, d), 10.00 (1H, 2 s); 19F NMR (376 MHz, d6-DMSO, proton-decoupled) δ −141.0, −156.9; M+H 585.1, M−H 583.2.

Example 11

(S,S)-3-[2-(3-Benzoylamino-2-oxo-2H-pyridin-1-yl)-butyrylamino]-4-oxo-5-(2,3,5,6-tetrafluoro-phenoxy)-pentanoic acid

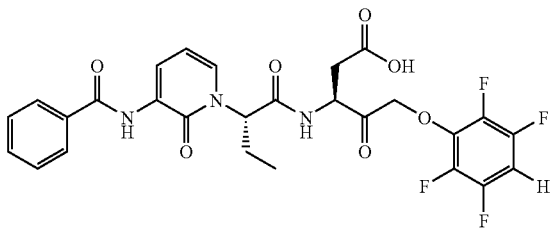

Prepared from (S)-2-(3-Amino-2-oxo-2H-pyridin-1-yl)-butyric acid tert-butyl ester and benzoyl chloride according to methods C-G; pink solid; IR (solid) 1645, 1509, 1490 cm−1; 1H NMR (400 MHz, d6-DMSO) δ 0.79-0.85 (3H, m), 1.95-1.99 (1H, m), 2.06-2.10 (1H, m), 2.60 (1H, dd), 2.77 (1H, dd), 4.59-4.63 (1H, m), 5.25 (2H, m), 5.42-5.55 (1H, m), 6.38-6.42 (1H, m), 7.51-7.62 (5H, m), 7.89-7.91 (2H, m), 8.27-8.31 (1H, m), 8.69-8.99 (1H, m), 9.28 (1H, m); 19F NMR (376 MHz, d6-DMSO, proton-decoupled) δ −140.6, −141.0, −156.9, −157.0; M+H 578.2, M−H 576.2.

Example 12

(S,S)-4-Oxo-3-[2-(2-oxo-3-phenylacetylamino-2H-pyridin-1-yl)-butyrylamino]-5-(2,3,5,6-tetrafluoro-phenoxy)-pentanoic acid

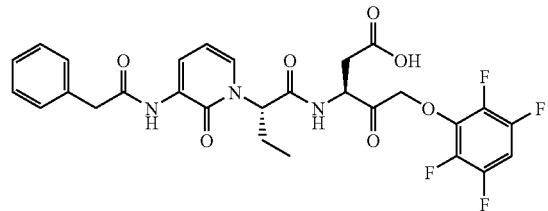

Prepared from (S)-2-(3-Amino-2-oxo-2H-pyridin-1-yl)-butyric acid tert-butyl ester and phenylacetyl chloride according to methods C-G; pink solid; IR (solid) 1659, 1635, 1519 cm−1; 1H NMR (400 MHz, d6-DMSO) δ 0.77 (3H, t), 1.85-1.96 (1H, m), 2.03-2.07 (1H, m), 2.59 (1H, dd), 2.71-2.77 (1H, m), 3.79 (2H, s), 4.61-4.66 (1H, m), 5.16-5.29 (2H, m), 5.35-5.44 (1H, m), 6.28 (1H, t), 7.24-7.39 (6H, m), 7.52-7.67 (1H, m), 8.19-8.21 (1H, m), 8.61-8.92 (1H, m), 9.28 (1H, br s); 19F NMR (376 MHz, d6-DMSO, proton-decoupled) δ −140.6, −141.0, −156.90, −157.0; M+H 592.2, M−H 590.2.

Example 13

(S,S)-3-[2-(3-Acetylamino-2-oxo-5-trifluoromethyl-2H-pyridin-1-yl)-butyrylamino]-4-oxo-5-(2,3,5,6-tetrafluoro-phenoxy)-pentanoic acid

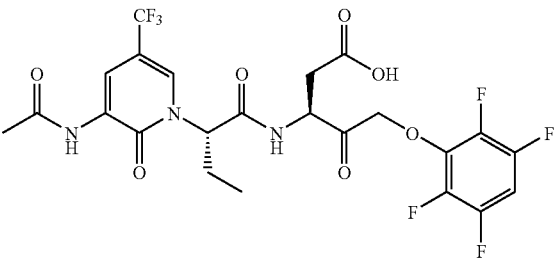

Prepared from (2-oxo-5-trifluoromethyl-1,2-dihydro-pyridin-3-yl)-carbamic acid benzyl ester according to methods A-G; white solid; IR (solid) 1659, 1514 cm−1; 1H NMR (400 MHz, d6-DMSO) δ 0.79 (3H, t), 2.07-2.33 (5H, m), 2.59-2.79 (2H, m), 4.59-4.63 (1H, m), 5.18-5.29 (2H, m), 5.41-5.45 (1H, m), 7.55-7.62 (1H, m), 7.89 (1H, s), 8.41-8.43 (1H, m), 9.04 (1H, d), 9.61-9.63 (1H, m); 19F NMR (376 MHz, d6-DMSO, proton-decoupled) δ −61.4, −140.7, −141.1, −156.8–156.9–157.02, −157.1; M+H 584.2, M−H 582.2.

Example 14

(S,S)-3-{2-[3-(3-Ethyl-ureido)-2-oxo-2H-pyridin-1-yl]-butyrylamino}-4-oxo-5-(2,3,5,6-tetrafluoro-phenoxy)-pentanoic acid

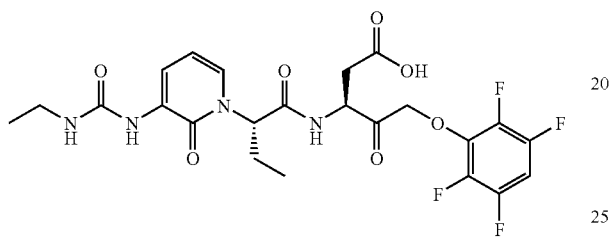

Prepared from (S)-2-(3-Amino-2-oxo-2H-pyridin-1-yl)-butyric acid tert-butyl ester and ethyl isocyanate according to methods C-G; pink solid; IR (solid) 1664, 1645, 1550, 1493, 1208 cm−1; 1H NMR (400 MHz, d6-DMSO) δ 0.80 (3H, t), 1.05 (3H, t), 1.80-2.20 (2H, m), 2.50-2.85 (2H, m), 3.15 (2H, m), 4.65 (1H, m), 5.25 (2H, dd), 5.40 (1H, m), 6.25 (1H, t), 7.15 (1H, s), 7.25 (1H, d), 7.60 (1H, m), 8.05 (1H, m), 8.20 (1H, s), 8.95 (1H, d); 19F NMR (376 MHz, d6-DMSO, proton-decoupled) δ −141.1, −156.9; M+H 545.2, M−H 543.2.

Example 15

(S,S)-3-{2-[3-(3,3-Diethyl-ureido)-2-oxo-2H-pyridin-1-yl]-butyrylamino}-4-oxo-5-(2,3,5,6-tetrafluoro-phenoxy)-pentanoic acid

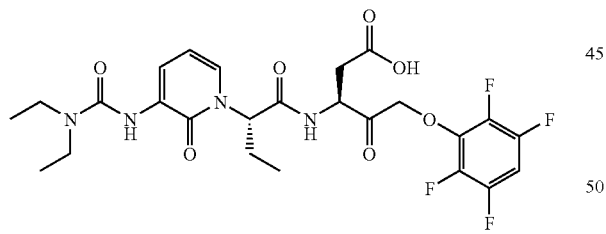

Method H:

To a cooled (0° C.) solution of (S)-2-(3-Amino-2-oxo-2H-pyridin-1-yl)-butyric acid tert-butyl ester (400 mg, 1.59 mmol) in dichloroethane (3 mL) was added triethylamine (0.254 mL, 1.82 mmol). This solution was added dropwise to a solution of diphosgene (0.11 mL, 0.91 mmol) in dichloroethane (7 mL) at 0° C. over 10 minutes. The reaction mixture was stirred at room temperature for 90 minutes and then partitioned between EtOAc and aqueous 1M HCl. The organic layer was washed with brine, dried (MgSO4), filtered and evaporated to afford the isocyanate as a brown oil.

To a cooled (0° C.) solution of the isocyanate prepared above (244 mg, 0.79 mmol) in dichloroethane (4 mL) was added triethylamine (0.122 mL, 0.87 mmol) followed by diethylamine (0.082 mL, 0.79 mmol). The reaction mixture was stirred at room temperature for 3 hours and then partitioned between EtOAc and aqueous 1M HCl. The organic layer was washed with brine, dried (MgSO4), filtered and evaporated to afford a brown oily residue which was purified by flash column chromatography (50% ethyl acetate/hexane) to afford the diethylurea as a colourless oil.

This intermediate was involved in the sequence described in methods D-G to afford the title compound; pink solid; IR (solid) 1640, 1512, 1213 cm−1; 1H NMR (400 MHz, d6-DMSO) δ 0.75-0.95 (3H, m), 1.10-1.40 (6H, m), 1.90-2.25 (2H, m), 2.60-2.90 (2H, m), 3.30-3.50 (4H, m), 4.75 (1H, m), 5.10-5.60 (3H, m), 6.35 (1H, t), 7.30 (1H, m), 7.75 (1H, m), 7.80 (1H, m), 8.05 (1H, m), 8.95-9.05 (1H, m); 19F NMR (376 MHz, d6-DMSO, proton-decoupled) δ −141.0, −156.9; M+H 573.3, M−H 571.2.

Example 16

(S,S)-4-Oxo-3-(2-{2-oxo-3-[(pyrrolidine-1-carbonyl)-amino]-2H-pyridin-1-yl}-butyrylamino)-5-(2,3,5,6-tetrafluoro-phenoxy)-pentanoic acid

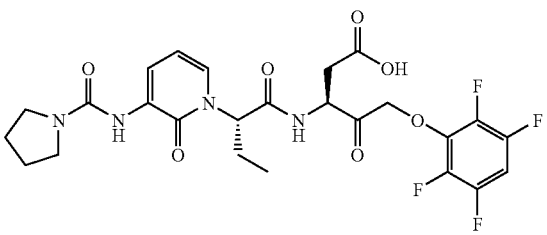

Prepared from (S)-2-(3-Amino-2-oxo-2H-pyridin-1-yl)-butyric acid tert-butyl ester and pyrrolidine according to methods H, D-G; pink solid; IR (solid) 1650, 1593, 1512, 1489, 1208 cm−1; 1H NMR (400 MHz, d6-DMSO) δ 0.80 (3H, m), 1.80-2.20 (6H, m), 2.60-2.90 (2H, m), 3.30-3.50 (4H, m), 4.60-4.75 (1H, m), 5.10-5.50 (3H, m), 6.30 (1H, t), 7.35 (1H, m), 7.50-7.75 (2H, m), 8.00 (1H, m), 8.85-8.95 (1H, m); 19F NMR (376 MHz, d6-DMSO, proton-decoupled) δ −141.1, −156.9; M+H 571.3, M−H 569.3.

Example 17

(S,S)-3-[2-(3-Methoxycarbonylamino-2-oxo-2H-pyridin-1-yl)-butyrylamino]-4-oxo-5-(2,3,5,6-tetrafluoro-phenoxy)-pentanoic acid

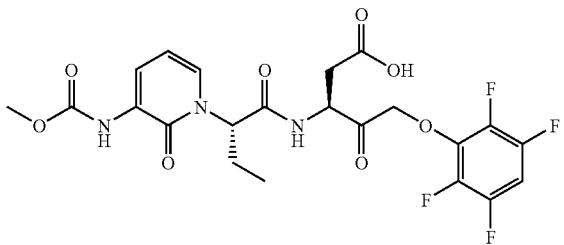

Prepared from (S)-2-(3-Amino-2-oxo-2H-pyridin-1-yl)-butyric acid tert-butyl ester and methyl chloroformate according to methods C-G; pink solid; IR (solid) 1644, 1661, 1709 cm−1; 1H NMR (400 MHz, d6-DMSO) δ 0.81 (3H, m), 1.95

(1H, m), 2.09 (1H, m), 2.50-2.98 (2H, m), 3.70 (3H, s), 4.20-5.50 (4H, m), 6.31 (1H, m), 7.40 (1H, m), 7.59 (1H, m), 7.82 (1H, m), 8.20 (1H, s), 8.55-9.00 (1H, d); $^{19}$F NMR (376 MHz, d6-DMSO, proton-decoupled) δ −140.6, −141.0, −141.1, −156.80, −156.9, −157.0, −157.1; M+H 532.3, M−H 530.3.

Example 18

(S,S)-3-[2-(3-Ethanesulfonylamino-2-oxo-2H-pyridin-1-yl)-butyrylamino]-4-oxo-5-(2,3,5,6-tetrafluoro-phenoxy)-pentanoic acid

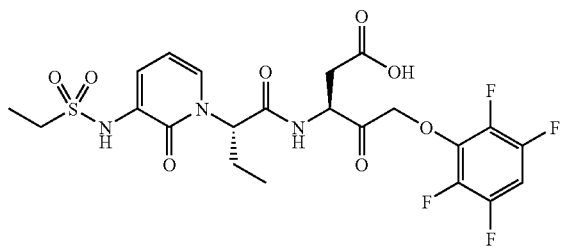

Prepared from (S)-2-(3-Amino-2-oxo-2H-pyridin-1-yl)-butyric acid tert-butyl ester and ethanesulfonyl chloride according to methods C-G; pink solid; $^1$H NMR (400 MHz, d6-DMSO) δ 0.74-0.82 (3H, m), 1.17-1.25 (3H, m), 1.85-2.10 (2H, m), 2.54-2.79 (2H, m), 3.09-3.15 (2H, m), 4.58-4.68 (1H, m), 5.13-5.38 (2H, m), 6.26-6.31 (1H, m), 7.34-7.38 (1H, m), 7.51-7.73 (2H, m), 8.72-8.76 (1H, m), 8.89-8.97 (1H, m), 12.51 (1H, br s); M+H 566.2, M−H 564.2.

Example 19

(S,S)-4-Oxo-3-{2-[2-oxo-3-(propane-1-sulfonylamino)-2H-pyridin-1-yl]-butyrylamino}-5-(2,3,5,6-tetrafluoro-phenoxy)-pentanoic acid

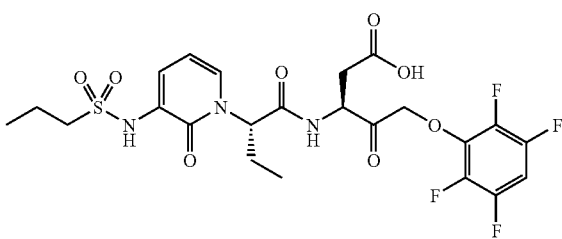

Prepared from (S)-2-(3-Amino-2-oxo-2H-pyridin-1-yl)-butyric acid tert-butyl ester and propanesulfonyl chloride according to methods C-G; pink solid; $^1$H NMR (400 MHz, d6-DMSO) δ 0.74-0.82 (3H, m), 0.88-0.94 (3H, m), 1.63-1.74 (2H, m), 1.85-2.10 (2H, m), 2.56-2.79 (2H, m), 3.06-3.13 (2H, m), 4.58-4.68 (1H, m), 5.13-5.40 (2H, m), 6.26-6.31 (1H, m), 7.34-7.37 (1H, m), 7.50-7.62 (2H, m), 8.71-8.75 (1H, m), 8.90-8.97 (1H, m), 12.53 (1H, br s); M+H 580.3, M−H 578.3.

Example 20

(S,S)-4-Oxo-3-{2-[2-oxo-3-(propane-2-sulfonylamino)-2H-pyridin-1-yl]-butyrylamino}-5-(2,3,5,6-tetrafluoro-phenoxy)-pentanoic acid

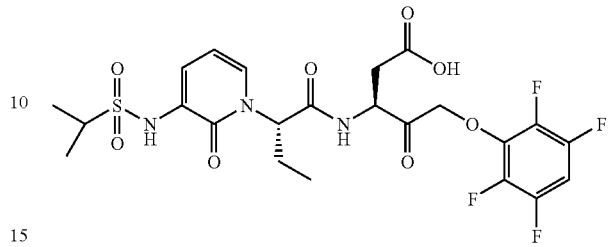

Prepared from (S)-2-(3-Amino-2-oxo-2H-pyridin-1-yl)-butyric acid tert-butyl ester and isopropylsulfonyl chloride using methods similar to C-G; pink solid; IR (solid) 1645, 1518 cm$^{-1}$; $^1$H NMR (400 MHz, d6-DMSO) δ 1.7-1.8 (3H, m), 1.18-1.25 (6H, m), 1.85-2.05 (2H, m), 2.55-2.8 (2H, m), 3.2-3.3 (1H, m), 4.52-4.62 (1H, m), 5.15-5.32 (3H, m), 5.4-5.43 (1H, m), 6.25 (1H, t), 7.3-7.35 (1H, m), 7.45-7.6 (2H, m), 8.6-8.7 (1H, m), 8.9-9.0 (1H, m); M+H 580.2, M−H 578.2.

Example 21

(S,S)-3-[2-(3-Benzenesulfonylamino-2-oxo-2H-pyridin-1-yl)-butyrylamino]-4-oxo-5-(2,3,5,6-tetrafluoro-phenoxy)-pentanoic acid

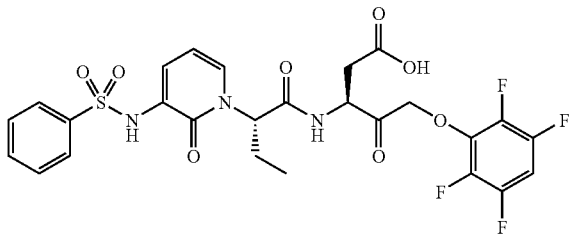

Prepared from (S)-2-(3-Amino-2-oxo-2H-pyridin-1-yl)-butyric acid tert-butyl ester and benzenesulfonyl chloride according to methods C-G; pink solid; $^1$H NMR (400 MHz, d6-DMSO) δ 0.55-0.66 (3H, m), 1.72-1.84 (1H, m), 1.91-2.01 (1H, m), 2.53-2.61 (1H, m), 2.68-2.76 (1H, m), 4.54-4.63 (1H, m), 5.06-5.32 (2H, m), 6.20-6.25 (1H, m), 6.98-7.86 (9H, m), 8.84-8.90 (1H, m), 9.40-9.45 (1H, m), 12.51 (1H, br s); M+H 614.1, M−H 612.1.

Example 22

(S,S)-3-[2-(3-Ethanesulfonylamino-2-oxo-5-trifluoromethyl-2H-pyridin-1-yl)-butyrylamino]-4-oxo-5-(2,3,5,6-tetrafluoro-phenoxy)-pentanoic acid

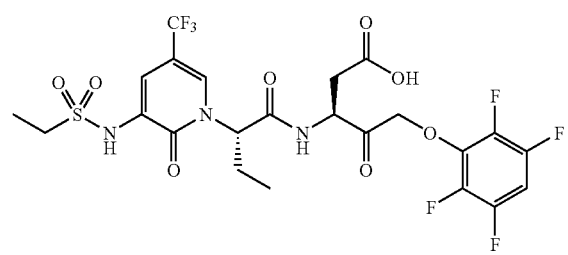

Prepared from (2-oxo-5-trifluoromethyl-1,2-dihydro-pyridin-3-yl)-carbamic acid benzyl ester according to methods A-G; off-white solid; IR (solid) 1664, 1519 cm$^{-1}$; $^1$H NMR (400 MHz, d6-DMSO) δ 0.78-0.87 (3H, m), 1.18-1.23 (3H, m), 1.99-2.14 (2H, m), 2.55-2.80 (2H, m), 3.19-3.25 (2H, m), 4.54-4.66 (1H, m), 5.20-5.30 (2H, m), 5.35-5.45 (1H, m), 7.47 (1H, m), 7.55-7.71 (1H, m), 8.01 (1H, s), 9.05 (1H, m), 9.31 (1H, s); $^{19}$F NMR (376 MHz, d6-DMSO, proton-decoupled) δ −63.11, −139.6, −157.1, −157.2; M+H 634.1, M−H 632.1.

Example 23

(S,S)-3-[3-Methyl-2-(2-oxo-3-phenylacetylamino-2H-pyridin-1-yl)-butyrylamino]-4-oxo-5-(2,3,5,6-tetrafluoro-phenoxy)-pentanoic acid

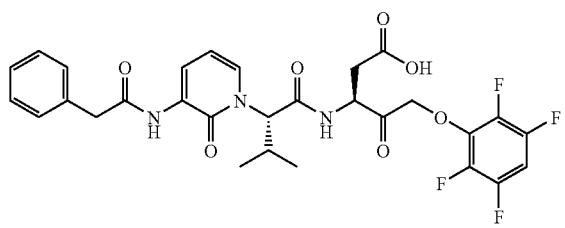

Prepared from (2-oxo-1,2-dihydro-pyridin-3-yl)-carbamic acid benzyl ester according to methods A-G; pink solid; IR (solid) 1644, 1683, 1740, 1791 cm−1; $^1$H NMR (400 MHz, d6-DMSO) δ 0.6 (3H, m), 1.0 (3H, m), 2.2-2.3 (1H, m), 2.5-3.0 (2H, m), 3.7-3.8 (2H, m), 4.1-5.4 (4H, m), 6.2-6.3 (1H, m), 7.2-7.4 (5H, m), 7.5-7.7 (2H, m), 8.1-8.2 (1H, m), 8.7-9.2 (2H, m); $^{19}$F NMR (376 MHz, d6-DMSO, proton-decoupled) δ −140.6, −141.0, −156.8, −157.0, −157.2; M+H 606.3, M−H 604.3.

Example 24

(S,S)-3-[2-(3-Ethanesulfonylamino-2-oxo-2H-pyridin-1-yl)-3-methyl-butyrylamino]-4-oxo-5-(2,3,5,6-tetrafluoro-phenoxy)-pentanoic acid

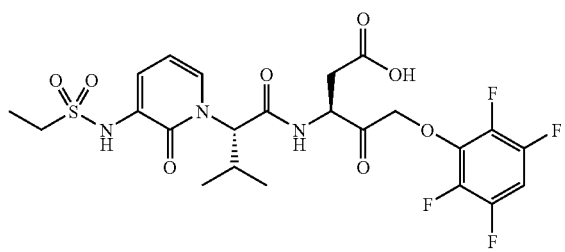

Prepared from (2-oxo-1,2-dihydro-pyridin-3-yl)-carbamic acid benzyl ester according to methods A-G; off-white solid; IR (solid) 1595, 1646, 1682, 1742, 1789 cm−1; $^1$H NMR (400 MHz, d6-DMSO) δ 0.7 (3H, m), 0.9-1.0 (3H, m), 1.2 (3H, m), 2.3 (1H, m), 2.6-3.0 (2H, m), 3.1 (2H, m), 4.1-5.4 (4H, m), 6.3 (1H, m), 7.3 (1H, m), 7.5-7.7 (2H, m), 8.7-9.2 (2H, m); $^{19}$F NMR (376 MHz, d6-DMSO, proton-decoupled) δ −140.6, −141.0, −156.7, −157.0, −157.1; M+H 580.2, M−H 578.3.

Example 25

(S)-5-Fluoro-4-oxo-3-[2-(2-oxo-3-propionylamino-2H-pyridin-1-yl)-propionylamino]-pentanoic acid

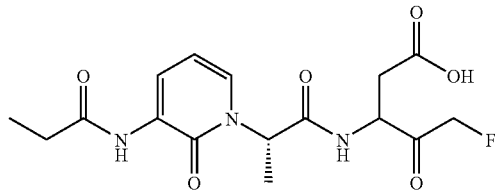

Prepared from (2-oxo-1,2-dihydro-pyridin-3-yl)-carbamic acid benzyl ester and 3-Amino-5-fluoro-4-hydroxy-pentanoic acid tert-butyl ester according to methods A-G; pink solid; IR (solid) 1643, 1658, 1711, 1740 cm−1; $^1$H NMR (400 MHz, d6-DMSO) δ 1.0-1.2 (3H, m), 1.4-1.6 (3H, m), 2.4-3.2 (4H, m), 4.2-4.6 (1.5H, m), 5.0-5.6 (2.5H, m), 6.3 (1H, m), 7.3 (1H, m), 8.2 (1H, m), 8.3-8.8 (1H, m), 9.1 (1H, m); $^{19}$F NMR (376 MHz, d6-DMSO, proton-decoupled) δ −226.8, −226.9, −230.6, −231.4, −232.7, −232.8; M+H 370.4, M−H 368.3.

Example 26

(S)-3-[2-(3-Benzoylamino-2-oxo-2H-pyridin-1-yl)-propionylamino]-5-fluoro-4-oxo-pentanoic acid

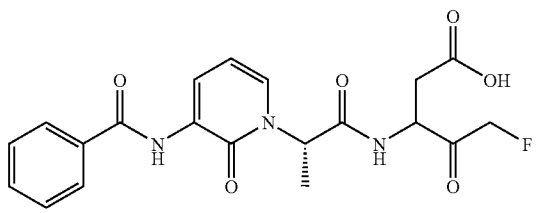

Prepared from (2-oxo-1,2-dihydro-pyridin-3-yl)-carbamic acid benzyl ester and 3-Amino-5-fluoro-4-hydroxy-pentanoic acid tert-butyl ester according to methods A-G; pink solid; IR (solid) 1523, 1644 cm−1; $^1$H NMR (400 MHz, d6-DMSO) δ 1.6 (3H, m), 2.5-3.2 (2H, m), 4.2-4.7 (1.5H, m), 5.0-5.6 (2.5H, m), 6.4 (1H, m), 7.4-7.6 (3H, m), 7.9 (2H, m), 8.3 (1H, m), 8.5-8.9 (1H, m), 9.3 (1H, m); $^{19}$F NMR (376 MHz, d6-DMSO, proton-decoupled) δ −226.7, −226.8, −230.4, −231.3, −232.8, −232.9; M+H 418.3, M−H 416.3.

Example 27

(S)-3-{2-[3-(2,6-Dichloro-benzoylamino)-2-oxo-2H-pyridin-1-yl]-propionylamino}-5-fluoro-4-oxo-pentanoic acid

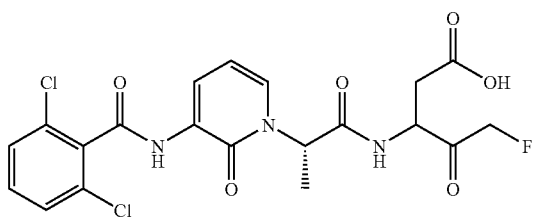

Prepared from (2-oxo-1,2-dihydro-pyridin-3-yl)-carbamic acid benzyl ester and 3-Amino-5-fluoro-4-hydroxy-pentanoic acid tert-butyl ester according to methods A-G; pink solid; IR (solid) 1521, 1646 cm−1; $^1$H NMR (400 MHz, d6-DMSO) δ 1.5-1.6 (3H, m), 2.5-3.2 (2H, m), 4.2-4.7 (1.5H, m), 5.0-5.5 (2.5H, m), 6.3-6.4 (1H, m), 7.4-7.5 (3H, m), 8.3 (1H, m), 8.5-8.9 (1H, m), 10.2 (1H, m); $^{19}$F NMR (376 MHz, d6-DMSO, proton-decoupled) δ −226.7, −226.8, −230.6, −231.4, −232.8, −232.9; M+H 486.3, M−H 484.3.

Example 28

(S)-5-Fluoro-4-oxo-3-[2-(2-oxo-3-phenylacety-lamino-2H-pyridin-1-yl)-propionylamino]-pentanoic acid

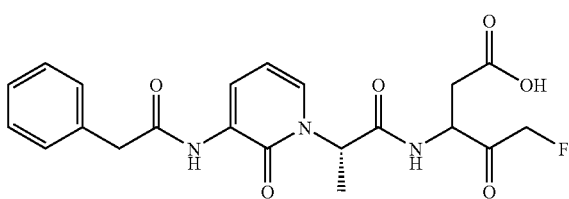

Prepared from (2-oxo-1,2-dihydro-pyridin-3-yl)-carbamic acid benzyl ester and 3-Amino-5-fluoro-4-hydroxy-pentanoic acid tert-butyl ester according to methods A-G; pink solid; IR (solid) 1524.2, 1652.4 cm−1; $^1$H NMR (400 MHz, d6-DMSO) δ 1.5 (3H, m), 2.5-3.2 (2H, m), 3.8 (2H, m), 4.2-4.7 (1.5H, m), 5.0-5.5 (2.5H, m), 6.3 (1H, m), 7.2-7.4 (6H, m), 8.2 (1H, m), 8.4-8.9 (1H, m), 9.3 (1H, m); $^{19}$F NMR (376 MHz, d6-DMSO, proton-decoupled) δ −226.7, −226.8, −230.6, −231.5, −232.8, −232.9; M+H 432.3, M−H 430.3.

Example 29

(S)-5-Fluoro-4-oxo-3-[2-(2-oxo-3-propionylamino-2H-pyridin-1-yl)-butyrylamino]-pentanoic acid

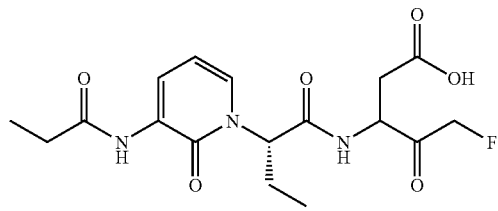

Prepared from (2-oxo-1,2-dihydro-pyridin-3-yl)-carbamic acid benzyl ester and 3-Amino-5-fluoro-4-hydroxy-pentanoic acid tert-butyl ester according to methods A-G; pink solid; IR (solid) 1644, 1585, 1518, 1214 cm−1; $^1$H NMR (400 MHz, d6-DMSO) δ 0.8-0.9 (3H, m), 1.05 (3H, t), 1.9-2.1 (2H, m), 2.4-2.5 (2H, m), 2.6-2.95 (2H, m), 4.2-4.5 (2H, m), 5.1-5.5 (3H, m), 6.3-6.35 (1H, m), 7.4-7.45 (1H, m), 8.2-8.25 (1H, m), 8.8-8.9 (1H, m), 9.1-9.15 (1H, m); $^{19}$F NMR (376 MHz, d6-DMSO, proton-decoupled) δ −226.7, −232.6; M+H 384.3, M−H 382.3.

Example 30

(S)-3-[2-(3-Benzoylamino-2-oxo-2H-pyridin-1-yl)-butyrylamino]-5-fluoro-4-oxo-pentanoic acid

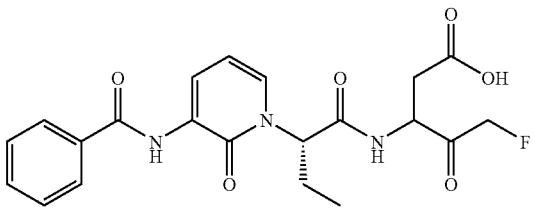

Prepared from (2-oxo-1,2-dihydro-pyridin-3-yl)-carbamic acid benzyl ester and 3-Amino-5-fluoro-4-hydroxy-pentanoic acid tert-butyl ester according to methods A-G; pink solid; IR (solid) 1643, 1522, 1204 cm−1; $^1$H NMR (400 MHz, d6-DMSO) δ 0.75-0.85 (3H, m), 1.9-2.2 (2H, m), 2.6-2.9 (2H, m), 4.3-4.7 (2H, m), 5.1-5.6 (2H, m6.4-6.5 (1H, m), 7.5-7.85 (4H, m), 7.9-8.0 (1H, m), 8.3-8.4 (1H, m), 8.85-8.95 (1H, m), 9.35 (1H, s); M+H 432.3, M−H 430.3.

Example 31

(S)-3-{2-[3-(2,6-Dichloro-benzoylamino)-2-oxo-2H-pyridin-1-yl]-butyrylamino}-5-fluoro-4-oxo-pentanoic acid

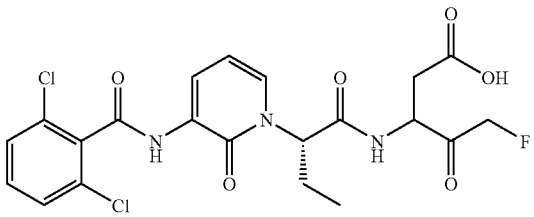

Prepared from (2-oxo-1,2-dihydro-pyridin-3-yl)-carbamic acid benzyl ester and 3-Amino-5-fluoro-4-hydroxy-pentanoic acid tert-butyl ester according to methods A-G; white solid; IR (solid) 1682, 1645, 1580, 1516, 1216 cm−1; $^1$H NMR (400 MHz, d6-DMSO) δ 0.8-0.9 (3H, m), 1.9-2.1 (2H, m), 2.6-2.85 (2H, m), 4.4-4.7 (2H, m), 5.1-5.5 (2H, m), 6.4-6.5 (1H, m), 7.5-7.6 (4H, m), 8.33-8.38 (1H, m), 8.85-8.95 (1H, m), 9.15-9.25 (1H, s); M+H 500.3, M−H 498.3.

Example 32

(S)-5-Fluoro-4-oxo-3-(2-{2-oxo-3-[(pyridine-2-carbonyl)-amino]-2H-pyridin-1-yl}-butyrylamino)-pentanoic acid

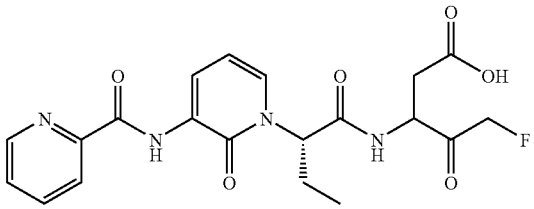

Prepared from (2-oxo-1,2-dihydro-pyridin-3-yl)-carbamic acid benzyl ester and 3-Amino-5-fluoro-4-hydroxy-pentanoic acid tert-butyl ester according to methods A-G; cream solid; IR (solid) 1685, 1644, 1521 cm−1; $^1$H NMR (400 MHz, d6-DMSO) δ 0.81-0.86 (3H, m), 1.90-2.05 (1H, m), 2.06-

2.19 (1H, m), 2.54-2.90 (2H, m), 4.58-4.72 (1H, m), 5.07-5.31 (2H, m), 5.42-5.57 (1H, m), 6.40-6.44 (1H, m), 7.47-7.49 (1H, m), 6.68-7.72 (1H, m), 8.09-8.11 (1H, m), 8.18 (1H, d), 8.45-8.47 (1H, m), 8.73-8.75 (1H, m), 8.87 (1H, dd), 10.74 (1H, s), 12.45 (1H, brd s); $^{19}$F NMR (376 MHz, d6-DMSO, proton-decoupled) δ −226.8, −230.4, −230.6, −231.0, −232.5, −232.6, −232.8, −232.9; M+H 433.4, M−H 431.4.

Example 33

(S)-5-Fluoro-4-oxo-3-[2-(2-oxo-3-phenylacetylamino-2H-pyridin-1-yl)-butyrylamino]-pentanoic acid

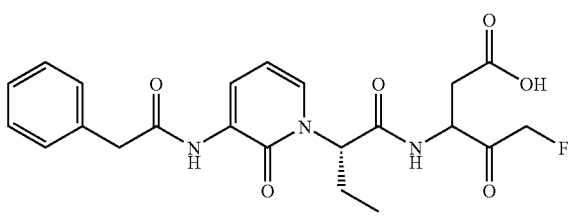

Prepared from (2-oxo-1,2-dihydro-pyridin-3-yl)-carbamic acid benzyl ester and 3-Amino-5-fluoro-4-hydroxy-pentanoic acid tert-butyl ester according to methods A-G; pink solid; IR (solid) 1644, 1672, 1742, 1785 cm−1; $^{1}$H NMR (400 MHz, d6-DMSO) δ 0.7-0.8 (3H, m), 1.8-2.2 (2H, m), 2.5-3.2 (2H, m), 3.8 (2H, s), 4.2-4.7 (2H, m), 5.1-5.5 (2H, m), 6.3 (1H, m), 7.2-7.4 (6H, m) 8.2 (1H, m), 8.5-9.4 (2H, m); $^{19}$F NMR (376 MHz, d6-DMSO, proton-decoupled) δ −226.7, −226.7, −230.4, −231.2, −232.6, −232.6; M+H 446.3, M−H 444.3.

Example 34

(S)-5-Fluoro-4-oxo-3-{2-[2-oxo-3-(2-m-tolyl-acetylamino)-2H-pyridin-1-yl]-butyrylamino}-pentanoic acid

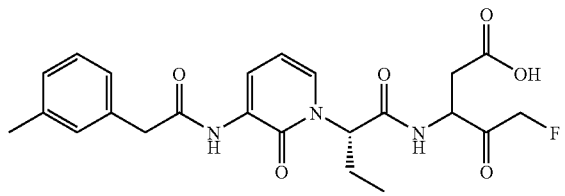

Prepared from (2-oxo-1,2-dihydro-pyridin-3-yl)-carbamic acid benzyl ester and 3-Amino-5-fluoro-4-hydroxy-pentanoic acid tert-butyl ester according to methods A-G; ochre solid; IR (solid) 1644, 1678 cm−1; $^{1}$H NMR (400 MHz, d6-DMSO) δ 0.7-0.8 (3H, m), 1.8-2.2 (2H, m), 2.3 (3H, s), 2.5-3.2 (2H, m), 3.7-3.8 (2H, s), 4.2-5.5 (4H, m), 6.3 (1H, m), 7.0-7.3 (4H, m), 7.4 (1H, m), 8.2 (1H, m), 8.5-8.9 (1H, m), 9.2-9.3 (1H, m); $^{19}$F NMR (376 MHz, d6-DMSO, proton-decoupled) δ −226.7, −226.7, −230.4, −231.2, −232.6, −232.7; M+H 460.3, M−H 459.4.

Example 35

(S)-5-Fluoro-4-oxo-3-[2-(2-oxo-3-propionylamino-2H-pyridin-1-yl)-pentanoylamino]-pentanoic acid

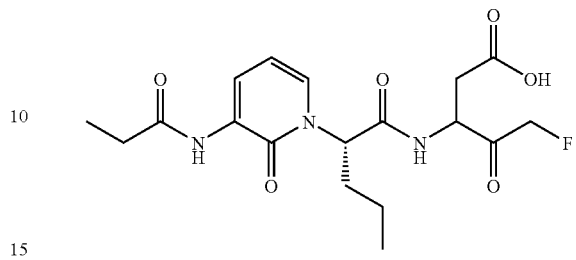

Prepared from (2-oxo-1,2-dihydro-pyridin-3-yl)-carbamic acid benzyl ester and 3-Amino-5-fluoro-4-hydroxy-pentanoic acid tert-butyl ester according to methods A-G; white solid; $^{1}$H NMR (400 MHz, d6-DMSO) δ 0 0.85-0.95 (3H, m), 1.0-1.1 (3H, m), 1.1-1.17 (2H, m), 1.9-2.0 (2H, m), 2.4-2.5 (2H, m), 2.6-2.90 (2H, m), 4.5-4.65 (1H, m), 5.1-5.5 (3H, m), 6.3-6.35 (1H, m), 7.4-7.43 (1H, m), 8.2-8.23 (1H, m), 8.8-8.9 (1H, m), 9.05-9.1 (1H, m); $^{19}$F NMR (376 MHz, d6-DMSO, proton-decoupled) δ −226.7, −232.6; M+H 398.4, M−H 396.4.

Example 36

(S)-5-Fluoro-3-[4-methyl-2-(2-oxo-3-propionylamino-2H-pyridin-1-yl)-pentanoylamino]-4-oxo-pentanoic acid

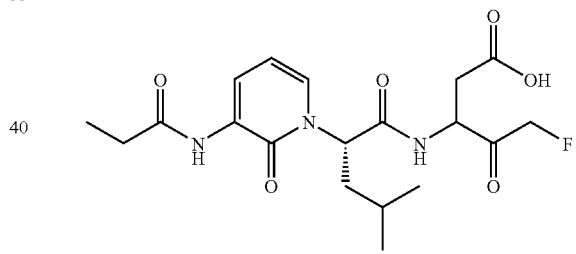

Prepared from (2-oxo-1,2-dihydro-pyridin-3-yl)-carbamic acid benzyl ester and 3-Amino-5-fluoro-4-hydroxy-pentanoic acid tert-butyl ester according to methods A-G; pink solid; $^{1}$H NMR (400 MHz, d6-DMSO) δ 0.85 (6H, m), 1.05 (3H, t), 1.30 (1H, m), 1.70-2.10 (2H, 2×m), 2.30-3.00 (4H, m), 4.60-4.80 (1H, m), 5.05-5.40 (2H, m), 5.65 (1H, m), 6.35 (1H, m), 7.45 (1H, m), 8.25 (1H, m), 8.95 (1H, m), 9.15 (1H, m); $^{19}$F NMR (376 MHz, d6-DMSO, proton-decoupled) δ −226.7, −232.5; M+H 412.3.

Livingston, et al., "In Vitro and In Vivo Studies of ICE Inhibitors," Journal of Cellular Biochemistry, 64:19-26 (1997).

Husain, et al., "Some New 2-Aryloxymethyl-3-alpha-substituted Carboxymethyl-6, 8-Substituted-4-quinazolones as Possible Anticonvulsants," Pharmazie, 37:408-410 (1982).

Hussain, et al., "Some Newer Quinazolones as Possible Anticonvulsants," J. Chem. Soc. Pak., 6(4):211-215 (1984).

Canonne, et al., "Synthesis of Chiral 3-Substituted 2,4 (1H, 3H)-Quinazolinediones," Heterocycles, 36(6):1305-1314 (1993).

Example 37

(S)-5-Fluoro-3-[2-(5-methyl-2-oxo-3-phenylacetylamino-2H-pyridin-1-yl)-butyrylamino]-4-oxo-pentanoic acid

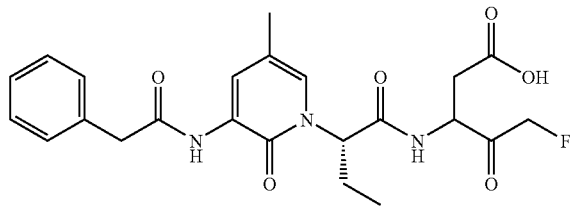

Prepared from (5-Methyl-2-oxo-1,2-dihydro-pyridin-3-yl)-carbamic acid benzyl ester and 3-Amino-5-fluoro-4-hydroxy-pentanoic acid tert-butyl ester according to methods A-G; yellow solid; IR (solid) 1654, 1741, 1785 cm−1; $^1$H NMR (400 MHz, d6-DMSO) δ 0.7-0.8 (3H, m), 1.8-2.2 (5H, m), 2.5-3.2 (2H, m), 3.8 (2H, s), 4.2-5.5 (4H, m), 7.1-7.4 (6H, m), 8.1 (1H, m), 8.4-8.9 (1H, m), 9.2-9.4 (1H, m); $^{19}$F NMR (376 MHz, d6-DMSO, proton-decoupled) δ −226.7, −226.7, −227.5, −230.5, −231.3, −232.6, −232.6, −233.4; M+H 460.4, M−H 458.4.

Example 38

(S,S)-4-Oxo-3-{2-[2-oxo-3-(thiazol-2-ylamino)-2H-pyridin-1-yl]-butyrylamino}-5-(2,3,5,6-tetrafluoro-phenoxy)-pentanoic acid

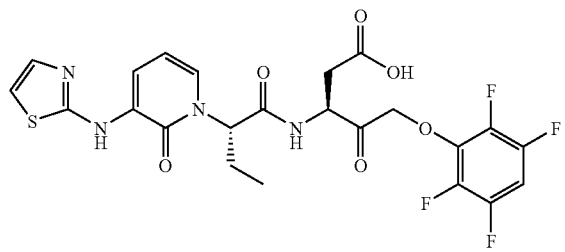

Method I:

3-(Thiazol-2-ylamino)-1H-pyridin-2-one

To a solution of 3-Amino-1H-pyridin-2-one (2.0 g, 18.7 mmol) in water (2 mL) was added 15% HCl (10 mL, 18 mmol) followed by ammonium thiocyanate (1.5 g, 18 mmol) and the mixture was heated to reflux for two hours. Upon cooling the intermediate thiourea was found to precipitate as a red-brown solid. The mixture was filtered and the solid washed with water (5 mL). To a solution of the thiourea (1.3 g, 7.7 mmol) in EtOH (20 mL) and water (5 mL) was added chloroacetaldehyde (2.3 mL), 16.4 mmol) and the mixture was heated to reflux for four hours. On cooling, the mixture was diluted with EtOAc (30 mL) and washed with 10% NaHCO$_3$ and brine. The organic phase was dried over MgSO$_4$ and concentrated in vacuo. The residue was purified by flash column chromatography (100% EtOAc) to afford the title compound as a pale green solid (1.43 g, 40%): $^1$H NMR (400 MHz, CDCl$_3$) δ 1.6 (1H, s), 6.45 (1H, t), 6.75 (1H, s), 7.05-7.10 (1H, m), 7.40-7.42 (1H, m), 8.35-8.5 (2H, m); M+H 194.1, M−H 192.1.

This intermediate was involved in the sequence described in methods A and B-G to afford the example 38 as a white solid; IR (solid) 1648, 1593, 1517, 1490 cm−1; $^1$H NMR (400 MHz, d6-DMSO) δ 0.75-0.85 (3H, t), 1.9-2.2 (2H, m), 2.6-2.8 (2H, m), 4.6-4.7 (1H, m), 5.2-5.3 (2H, m), 5.35-5.45 (1H, m), 6.3-6.35 (1H, m), 6.96-6.98 (1H, m), 7.2-7.3 (2H, m), 7.5-7.65 (1H, m), 8.4-8.43 (1H, m), 8.8-8.9 (1H, 2×d), 9.9 (1H, br s), 12.5 (1H, brd s); $^{19}$F NMR (376 MHz, d6-DMSO, proton-decoupled) δ −141.0, −156.9; M+H 557.2, M−H 555.2.

Example 39

(S,S)-4-Oxo-3-[2-(2-oxo-3-propylamino-2H-pyridin-1-yl)-butyrylamino]-5-(2,3,5,6-tetrafluoro-phenoxy)-pentanoic acid

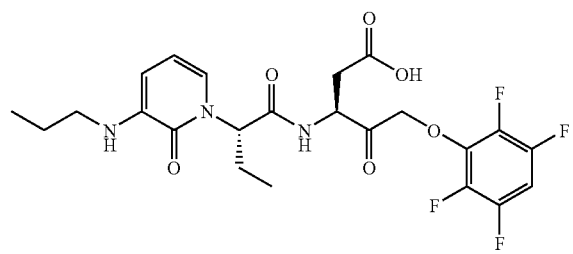

Method J:

(S)-2-[3-(Benzyloxycarbonyl-propyl-amino)-2-oxo-2H-pyridin-1-yl]-butyric acid tert-butyl ester

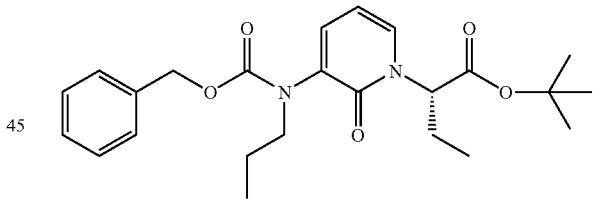

To a solution of (S)-2-(3-Benzyloxycarbonylamino-2-oxo-2H-pyridin-1-yl)-butyric acid tert-butyl ester (100 mg, 0.26 mmol) in anhydrous DMF (3 mL) was added NaH (60% dispersion, 10 mg, 0.26 mmol) and the reaction was stirred at ambient temperature for 30 minutes. Propyliodide (30 μL, 0.31 mmol) was added dropwise and the reaction stirred at ambient temperature overnight. The mixture was concentrated in vacuo to a solid and partitioned between EtOAc (10 mL) and water (10 mL). The organic layer was separated, dried over MgSO$_4$, and concentrated in vacuo. The residue was purified by flash column chromatography (30% EtOAc/hexane) to afford the title compound as a pale green solid (1.43 g, 40%): $^1$H NMR (400 MHz, CDCl$_3$) δ 0.85-0.95 (6H, m), 1.35 (9H, s), 1.55-1.65 (2H, m), 1.85-1.95 (1H, m), 2.20-2.27 (1H, m), 3.6-3.7 (2H, m), 5.15-5.2 (2H, m), 5.5-5.6 (1H, m), 6.25 (1H, t), 7.25-7.45 (7H, m); M+H 429.4.

This intermediate was involved in the sequence described in methods C-G and finally subjected to hydrogenolysis as described in method B to afford example 39 as an off-white solid; IR (solid) 1581, 1517, 1489, 938 cm−1; $^1$H NMR (400 MHz, d6-DMSO) δ 0.80 (3H, t), 0.9 (3H, t), 1.5-1.6 (2H, m), 1.8-2.05 (2H, m), 2.5-2.7 (2H, m), 2.9-3.0 (2H, m), 4.6-4.7 (1H, m), 5.1-5.4 (3H, m), 6.1-6.2 (2H, m), 6.85-6.9 (1H, m), 7.5-7.65 (1H, m), 8.7-8.90 (1H, 3×d), 12.5 (1H, brd s); M+H 516.2, M−H 514.2.

Example 40

Enzyme Assays

The assays for caspase inhibition are based on the cleavage of a fluorogenic substrate by recombinant, purified human Caspases-1, -3, or -8. The assays are run in essentially the same way as those reported by Garcia-Calvo et al. (J. Biol. Chem. 273 (1998), 32608-32613), using a substrate specific for each enzyme. The substrate for Caspase-1 is Acetyl-Tyr-Val-Ala-Asp-amino-4-methylcoumarin. The substrate for Caspases-3 and -8 is Acetyl-Asp-Glu-Val-Asp-amino-4-methylcoumarin. Both substrates are known in the art.

The observed rate of enzyme inactivation at a particular inhibitor concentration, $k_{obs}$, is computed by direct fits of the data to the equation derived by Thornberry et al. (Biochemistry 33 (1994), 3943-3939) using a nonlinear least-squares analysis computer program (PRISM 2.0; GraphPad software). To obtain the second order rate constant, $k_{inact}$, $k_{obs}$ values are plotted against their respective inhibitor concentrations and $k_{inact}$ values are subsequently calculated by computerized linear regression.

Inhibition of caspases-1, -3, and -8 activity for selected compounds of this invention was determined by the above method. Compounds 1-39 inhibited caspase-1 with a $k_{inact}$ of >200,000 (M$^{-1}$s$^{-1}$), caspase-3 with a $k_{inact}$ of at >50,000 ($k_{inact}$ (M$^{-1}$s$^{-1}$), and caspase-8 with a $k_{inact}$ of at >50,000 ($k_{inact}$ (M$^{-1}$s$^{-1}$).

Example 41

Inhibition of IL-1β Secretion from Whole Blood

Human blood is freshly drawn from healthy donors and diluted 1:2 in PBS. To 500 μl of diluted blood 50 ml of prediluted test compound in RPMI medium and 10 ml LPS (5 ng/ml final concentration on the plate) are added (LPS, Serotype 0111:B4, Sigma L3012). After stimulation for 18 hours supernatants are collected and assayed for IL-1β levels using the appropriate ELISA kit (R&D systems).

Table 2 below shows inhibition of IL-1β secretion from human whole blood for selected compounds of this invention as determined individually by the above methods.

TABLE 2

| Inhibition of IL-1β secretion | |
| --- | --- |
| Compound Number | IC$_{50}$ (μM) |
| 1, 2, 3, 5, 7, 10, 11, 14, 17, & 29 | <0.5 |
| 4, 6, 8, 9, 12, 13, 15, 16, 18, 19, 20, 21, 22, 23, 28., 36, 38, & 39 | 0.5-5 |

Example 42

Hypoxia-Induced Apoptosis of Rat Cortical Neurons

Cortical neurons are dissociated from Wistar rat embryos (E17) by a modification of the procedure of Rogers et al. 1997, Brain Res. Bulletin, 44:131. Briefly, cerebral cortices are isolated aseptically from 15-20 Wistar rat embryos. A cell suspension is prepared by mincing the cerebral cortices and digesting them with papain. Cells are washed with ovomucoid enzyme inhibitor and DNaseI and plated onto Poly-D lysine coated plates in high glucose DMEM containing 10% heat-inactivated fetal calf serum, L-glutamine, penicillin and streptomycin. The yield of neurons is 10×7 per embryo and they are 80-90% viable as assessed by Trypan blue exclusion.

The neurons are cultured in complete medium at 37° C. in a normal atmosphere for 48 hours prior to the hypoxia experiments. For hypoxia, the normal cell medium is replaced by oxygen-depleted serum-free medium. Cells are incubated in an atmosphere of 95% N2/5% CO2 for various lengths of time. Compounds are dissolved in DMSO at 100 mM then diluted in medium and added to the culture from time=0. The level of apoptosis is measured using a Cell Death Detection ELISA kit (Roche) which detects DNA fragmentation. Plates are read at 405 nm. Controls included cells cultured in aerobic conditions in serum-containing medium (+serum) and cells cultured in aerobic conditions in serum-deprived medium (−serum).

Table 3 shows the results of the activity of selected compounds of this invention tested individually in the Hypoxia-induced apoptosis of rat cortical neurons.

TABLE 3

| Activity in Hypoxia-induced Apoptosis Assay | |
| --- | --- |
| Compound Number | IC$_{50}$ (μM) |
| 2, 5, 10, 11, 12, 13, 15, 17, 20, 22, 38, & 39 | <1 |
| 1, 3, 4, 6, 7, 8, 9, 14, 16, 18, 19, 21, 24, 29, 30, 31, 34, 35, 36 & 37 | 1-10 |

Example 43

Anti-Fas Induced Apoptosis Assay

Cellular apoptosis may be induced by the binding of Fas ligand (FasL) to its receptor, CD95 (Fas). CD95 is one of a family of related receptors, known as death receptors, which can trigger apoptosis in cells via activation of the caspase enzyme cascade. The process is initiated by the binding of the adapter molecule FADD/MORT-1 to the cytoplasmic domain of the CD-95 receptor-ligand complex. Caspase-8 then binds FADD and becomes activated, initiating a cascade of events that involve the activation of downstream caspases and subsequent cellular apoptosis. Apoptosis can also be induced in cells expressing CD95 e.g., the Jurkat E6.1 T cell lymphoma cell line, using an antibody, rather than FasL, to crosslink the cell surface CD95. Anti-Fas-induced apoptosis is also triggered via the activation of caspase-8. This provides the basis of a cell based assay to screen compounds for inhibition of the caspase-8-mediated apoptotic pathway.

Experimental Procedure

Jurkat E6.1 cells are cultured in complete medium consisting of RPMI-1640 (Sigma No)+10% foetal calf serum (Gibco BRL No. 10099-141)+2 mM L-glutamine (Sigma No. G-7513). The cells are harvested in log phase of growth. 100 ml of cells at 5-8×105 cells/ml are transferred to sterile 50 ml Falcon centrifuge tubes and centrifuged for 5 minutes at 100×g at room temperature. The supernatant is removed and the combined cell pellets resuspended in 25 ml of complete medium. The cells are counted and the density adjusted to 2×106 cells/ml with complete medium.

The test compound is dissolved in dimethyl sulfoxide (DMSO)(Sigma No. D-2650) to give a 100 mM stock solution. This is diluted to 400 μM in complete medium, then serially diluted in a 96-well plate prior to addition to the cell assay plate.

100 μl of the cell suspension (2×106 cells) is added to each well of a sterile 96-well round-bottomed cluster plate (Costar No. 3790). 50 μl of compound solution at the appropriate dilution and 50 μl of anti-Fas antibody, clone CH-11 (Upstate, Cat No. 1 544 675) at a final concentration of 10 ng/ml, are added to the wells. Control wells are set up minus antibody and minus compound but with a serial dilution of DMSO as vehicle control. The plates are incubated for 16-18 hrs at 37° C. in 5% CO2 and 95% humidity.

Apoptosis of the cells is measured by the quantitation of DNA fragmentation using a 'Cell Death Detection Assay' from Roche diagnostics, No. 1544 675. After incubation for 16-18 hrs the assay plates are centrifuged at 100×g at room temperature for 5 minutes. 150 μl of the supernatant are removed and replaced by 150 μl of fresh complete medium. The cells are then harvested and 200 μl of the lysis buffer supplied in the assay kit are added to each well. The cells are triturated to ensure complete lysis and incubated for 30 minutes at 4° C. The plates are then centrifuged at 1900×g for 10 minutes and the supernatants diluted 1:20 in the incubation buffer provided. 100 μl of this solution is then assayed according to the manufacturer's instructions supplied with the kit. OD405 nm is measured 20 minutes after addition of the final substrate in a SPECTRAmax Plus plate reader (Molecular Devices). OD405 nm is plotted versus compound concentration and the IC50 values for the compounds are calculated using the curve-fitting program SOFTmax Pro (Molecular Devices) using the four parameter fit option.

Selected compounds have been tested in this assay and shown to inhibit Fas-induced apoptosis of Jurkat cells with IC50 values between 0.001 μM and 0.15 μM.

TABLE 4

| Activity in FAS-induced Apoptosis Assay | |
|---|---|
| Compound Number | IC$_{50}$ (μM) |
| 1, 2, 4, 5, 7, 11, 13, 17, 18, 19, 22, 25, 27, 29, 30, 31, 32, 33, 34, 35, 37 | <0.5 |
| 26, 28, 36 | 0.5-2 |

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments that have been represented by way of example above.

We claim:
1. A compound of formula I:

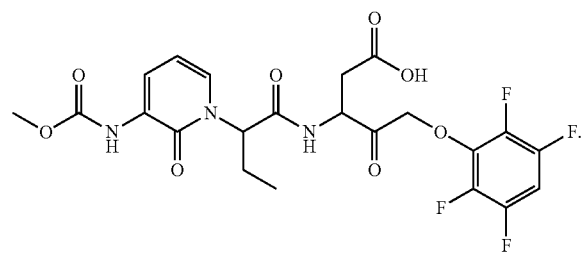

2. A pharmaceutical composition comprising:
a) a compound according to claim 1; and
b) a pharmaceutically acceptable carrier, adjuvant or vehicle.

3. A process for preparing a compound of formula (I):

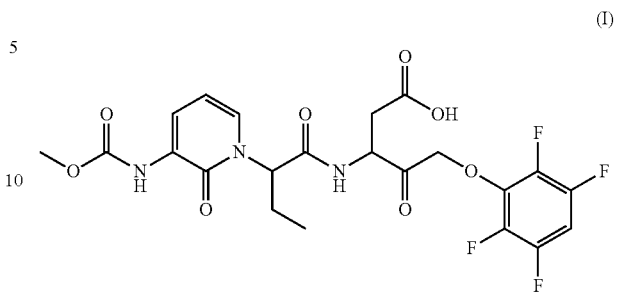

comprising:
(a) reacting a compound of formula (III):

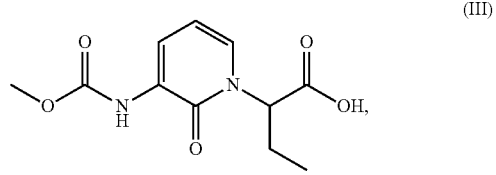

with a compound of formula (IV):

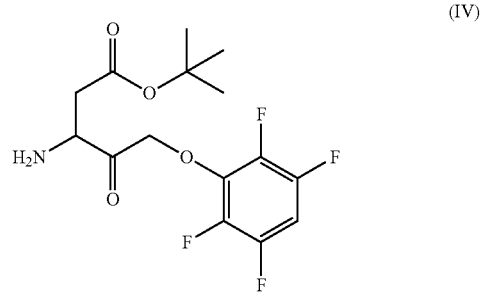

in the presence of coupling conditions and a solvent.

4. The process according to claim 3, wherein the compound of formula (III):

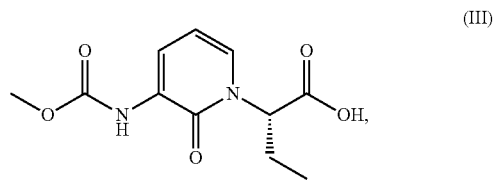

is prepared by a process comprising:
(c) reacting a compound of formula (V):

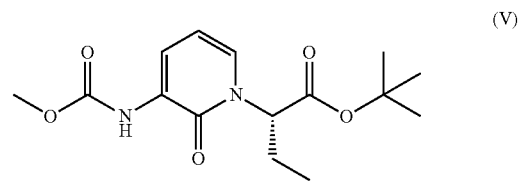

in a solvent in the presence of deprotecting conditions.

5. The process according to claim 4, wherein the compound of formula (V):

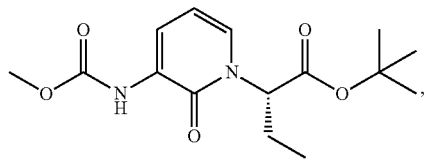
(V)

is prepared by a process comprising:
(d) reacting a compound of formula (VI):

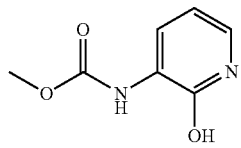
(VI)

with a compound of formula (VII):

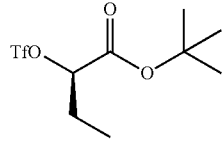
(VII)

in the presence of a solvent and a base.

6. A process for preparing a compound of formula (VIII):

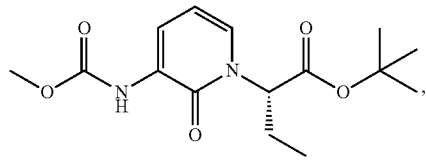
(VIII)

comprising the step of (e) reacting a compound of formula (IX):

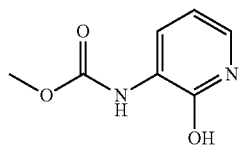
(IX)

with a compound of formula (VII):

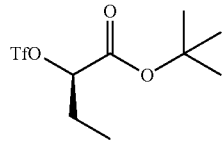
(VII)

in the presence of a solvent and a base.)

7. A process for preparing a compound of formula (I):

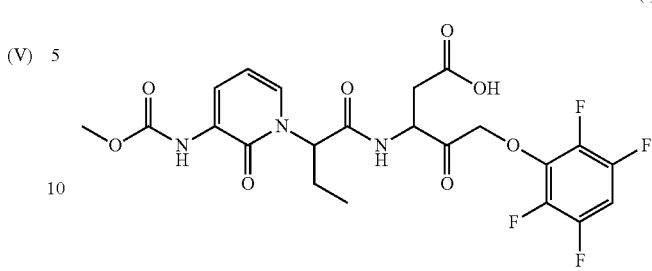
(I)

comprising:
(a) reacting a compound of formula (III):

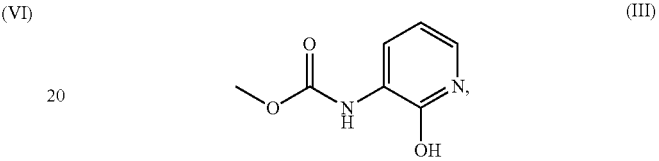
(III)

with a compound of formula (X):

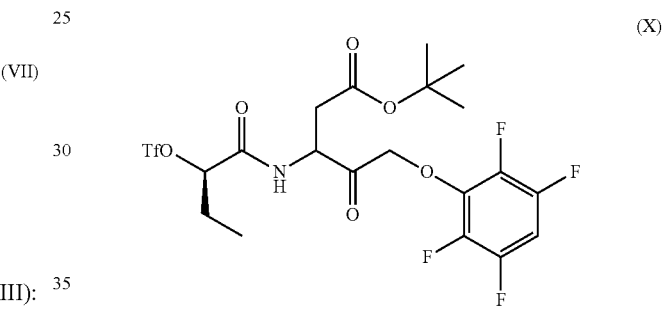
(X)

in the presence of coupling conditions and a solvent.

8. The compound of claim 1, as represented by formula Ib:

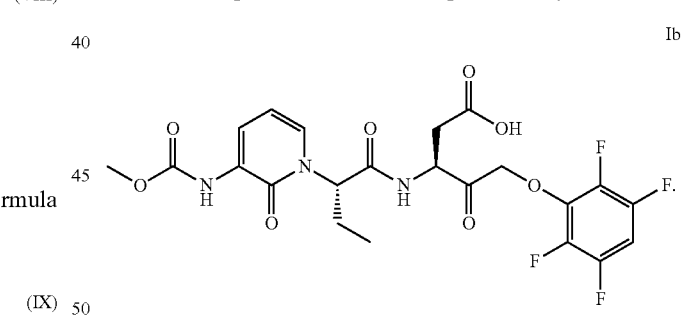
Ib

9. The compound of claim 1, as represented by formula Ia:

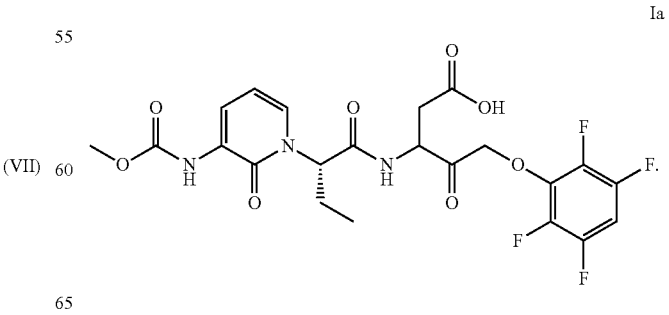
Ia